United States Patent
Ramasubramanian et al.

(10) Patent No.: US 10,465,227 B2
(45) Date of Patent: *Nov. 5, 2019

(54) MICROBIAL TESTING DEVICES, METHODS OF MAKING MICROBIAL TESTING DEVICES AND METHODS OF IDENTIFYING NOVEL ANTIMICROBIAL DRUG CANDIDATES

(71) Applicant: BOARD OF REGENTS, THE UNIVERSITY OF TEXAS SYSTEM, Austin, TX (US)

(72) Inventors: Anand K. Ramasubramanian, San Antonio, TX (US); Jose L. Lopez-Ribot, San Antonio, TX (US); Anand Srinivasan, San Antonio, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 935 days.

This patent is subject to a terminal disclaimer.

(21) Appl. No.: 14/603,873

(22) Filed: Jan. 23, 2015

(65) Prior Publication Data

US 2015/0167046 A1 Jun. 18, 2015

Related U.S. Application Data

(63) Continuation of application No. 13/522,446, filed as application No. PCT/US2011/021407 on Jan. 14, 2011, now Pat. No. 8,962,531.

(60) Provisional application No. 61/295,428, filed on Jan. 15, 2010, provisional application No. 62/022,258, filed on Jul. 9, 2014.

(51) Int. Cl.
| | |
|---|---|
| *C12Q 1/18* | (2006.01) |
| *C12Q 1/02* | (2006.01) |
| *C40B 60/00* | (2006.01) |
| *G01N 33/569* | (2006.01) |

(52) U.S. Cl.
CPC ......... *C12Q 1/18* (2013.01); *G01N 33/56961* (2013.01)

(58) Field of Classification Search
CPC combination set(s) only.
See application file for complete search history.

(56) References Cited

U.S. PATENT DOCUMENTS

| | | | |
|---|---|---|---|
| 5,474,915 A | 12/1995 | Dordick | |
| 5,618,933 A | 4/1997 | Dordick et al. | |
| 5,854,030 A | 12/1998 | Dordick et al. | |
| 7,267,958 B2 | 9/2007 | Dordick et al. | |
| 2002/0025537 A1 | 2/2002 | Bylina et al. | |
| 2002/0160444 A1 | 10/2002 | Reynolds et al. | |
| 2006/0073470 A1 | 4/2006 | Noda et al. | |
| 2007/0042453 A1* | 2/2007 | Novak | C12Q 1/18 435/32 |
| 2008/0166753 A1* | 7/2008 | Storey | C12Q 1/18 435/32 |

FOREIGN PATENT DOCUMENTS

| | | | |
|---|---|---|---|
| EP | 0242305 | 10/1987 | |
| WO | WO-2007053561 A2 * | 5/2007 | ......... G01N 33/5014 |

OTHER PUBLICATIONS

Pierce et al., A Simple and Reproducible 96 Well Plate-Based Method for the Formation of Fungal Biofilms and its Application to Antifungal Susceptibility Testing, Nat. Protoc., 2008, 3(9), 1494-1500.

DiDone et al., a Novel Assay of Biofilm Antifungal Activity Reveals That Amphotericin Band Caspofungin Lyse Candida Alibicans Cells in Biofilms, Yeast, 2011, 28, 561-568.

BD Diagnostic Systems, Instructions for Use—Ready-to-Use Bottled Media, 2003, 1-3.

Uppuluri et al., Dispersion as an Important Step in the Candida albicans Biofilm Development Cycle, PLoS Pathogens, 2010, 6(3), 1-13.

Eun, Ye-Jin and Weibel, Douglas B. (2009) "Fabrication of microbial biofilm arrays by geometric control of cell adhesion" Langmuir 25 {8), 4643-4654.

Jagnow, Jennifer and Clegg, Steven. (2003) "Klebsiella pneumoniae MrkD-mediated biofilm formation on extracellular matrix- and collagen-coated surfaces" Microbiology, 149, 2397-2405.

Xu, Tao, et al. {2004) "Construction of high-density bacterial colony arrays and patterns by the ink-jet method" Biotechnology and bioengineering 85 (1 ), 29-33.

International Search Report for PCT Application No. PCT/US2011/021407 dated Sep. 26, 2011.

Written Opinion for PCT Application No. PCT/US2011/021407 dated Sep. 26, 2011.

International Preliminary Report on Patentability for PCT Application No. PCT/US2011/021407 dated Jul. 17, 2012.

* cited by examiner

*Primary Examiner* — Amy M Bunker
(74) *Attorney, Agent, or Firm* — Thomas | Horstemeyer, LLP

(57) ABSTRACT

The present disclosure provides for microbial testing devices, methods for making microbial testing devices, methods for growing and testing microbial cultures and methods for testing compounds for antimicrobial activity.

18 Claims, 8 Drawing Sheets
(7 of 8 Drawing Sheet(s) Filed in Color)

MICROBIAL TESTING DEVICES, METHODS OF MAKING MICROBIAL TESTING DEVICES AND METHODS OF IDENTIFYING NOVEL ANTIMICROBIAL DRUG CANDIDATES

CROSS-REFERENCE TO RELATED APPLICATIONS

This application is a Continuation-in-Part application of co-pending U.S. Patent application entitled "Development Of A High-Throughput Screen for the Identification of Novel Antifungal Drug Candidates" having Ser. No. 13/522,446, filed on Oct. 15, 2012, which claims priority to International Application No. PCT/US2011/021407 of the same title filed on Jan. 14, 2011, which claims priority to U.S. provisional application of the same title having Ser. No. 61/295,428, filed on Jan. 15, 2010. This application also claims priority to U.S. provisional application entitled, "Development Of A High-Throughput Screen for the Identification of Novel Antifungal Drug Candidates," having Ser. No. 62/022,258, filed on Jul. 9, 2014, which is also entirely incorporated herein by reference.

STATEMENT REGARDING FEDERALLY SPONSORED RESEARCH OR DEVELOPMENT

This invention was made with Government support under grant number DE017294 awarded by the National Institutes Health. The Government has certain rights in this invention.

BACKGROUND

Nosocomial (hospital acquired) infections are the fourth leading cause of death in the U.S. with 2 million cases and more than $5 billion in added medical cost per annum. Each year approximately 10% of all patients admitted to hospitals in the U.S will develop a health-care associated infection, which translates to 2-4 million nosocomial infections, representing the eighth leading cause of death in the US, accounting for approximately 50,000 deaths annually. Other infections, such as those in the burns and wounds, also add significant morbidity and costs. Antibiotic therapy remains the mainstay for the treatment of infection; however, its success is severely threatened by the increasingly frequent development of resistance and the emergence of new microorganisms for which effective antibiotic therapies simply do not exist. To make matters worse, the antibiotic pipeline in most major pharmaceutical companies is drying up. One of the impediments to the rapid development of newer antibiotics is the fact that classical microbiological culture techniques are not compatible with modern methodologies for drug discovery that are dominated by high throughput screening (HTS) and its "hunger for speed".

A large number of these nosocomial infections are fungal infections, and are often associated with implantable devices, intravascular and urinary catheters, orthopedic implants, and intrauterine contraceptive devices, which is an $180 b per year industry. Fungal infections can be lethal as seen by mortality rates—50% for candidiasis, 90% for aspergillosis, and 100% for zygomycosis. For example, in pediatric patients, candidiasis (the most common fungal infection) is associated with a 10.0% increase in mortality, a mean 21.1-day increase in length of stay, and a mean increase in total per-patient hospital charges of $92,266. Similarly, in adult patients candidiasis is associated with a 14.5% increase in mortality, a mean 10.1-day increase in length of stay, and a mean increase in hospital charges of $39,331. Overall, these numbers suggests that despite having a market of $3.1b per year, which is ~10% of all anti-infectives, currently used antifungals are still ineffective. There are no new effective drugs in sight, and the antifungal pipeline is mostly dry. One of the reasons for poor efficacy of antifungal treatments is that many fungal organisms grow as 'biofilms' on surfaces of implantable medical devices, and the biofilms are significantly less susceptible to antifungal drugs compared to free-floating or planktonic cells. Biofilm infections are notoriously difficult to treat, and they commonly manifest as chronic or recurrent infections, and constitute a number of clinical challenges Evidence also shows that a large percentage of these hospital acquired infections are polymicrobial in nature. Many such mixed microbial infections also involve the formation of microbial biofilms. Biofilms are complex three-dimensional structures, which are composed of different morphological forms of the microbial organism including yeast, pseudohyphae and hyphae, in an extracellular matrix. The antifungal/antibacterial resistance of biofilms is primarily attributed to changes in genetic, physiological and molecular characteristics of the cells in the biofilm, and secondarily to slow diffusion of drugs, and the binding of drugs to the biofilm matrix. Thus, there is a need to develop new strategies for the screening and discovery of antimicrobial drugs (antifungals, antibacterials, antivirals, mixed anti-microbials, etc.) that prevent or control the growth of microbial organisms and/or the formation of biofilms.

The current industry standard is a 96-well plate assay, which, when invented in 2001 was revolutionary and it changed the way fungal biofilms were examined. Prior to 2001, growth and characterization of fungal biofilms was an ordeal and was performed by only a handful of investigators primarily by forming one biofilm at a time. However, practical considerations of time, cost and reagent volume severely limit the use of 96-well plate assays for probing diverse set of chemical libraries containing tens of thousands of molecules for new drugs, and novel, innovative technologies are sorely needed.

SUMMARY

Briefly described, embodiments of the present disclosure provide devices, systems, and methods for growth and screening microbial cultures for potential antimicrobial compounds and methods and devices for identifying new potential antimicrobial drugs. In embodiments the microbial cultures can include, but are not limited to, fungal cultures, bacterial cultures, and mixed microbial cultures.

Embodiments of microbial testing devices of the present disclosure include a flat substrate having a flat surface, an adhesion material coupled to the flat surface, and a plurality of spatially distinct, three-dimensional culture spots disposed on the adhesion material. The culture spots include a mixture of microbial cells, a matrix material containing a hydrogel, and an initial amount of growth medium, where the microbial cells in the culture spots are capable of remaining viable for at least 24 hrs without exposing the spots on the substrate to additional growth media.

Embodiments of methods of the present disclosure for testing a compound for antimicrobial activity include providing a testing device of the present disclosure; culturing the microbial cells in the spots without submerging the spots on the substrate in additional growth media, where the microbial cells are capable of remaining viable for at least 24 hours without exposing the spots on the substrate to additional growth media; exposing the compound to the spots on the device; and monitoring the spots for antimicrobial activity. In such methods, the testing device includes a flat substrate having a flat surface and a plurality of spatially distinct, three-dimensional culture spots disposed on the flat surface of the substrate, where the culture spots include a mixture of one or more species of microbial cells, a matrix material, and a growth medium. In embodiments of the methods of the present disclosure for testing a compound for antimicrobial activity, one or more test compounds is allowed to interact with one or more spatially distinct fungal cultures disposed on the substrate.

The present disclosure also provides methods of making a microbial testing device. In embodiments, such methods include obtaining a substrate having a flat surface; spotting a mixture including one or more types of microbial cells, a matrix material, and a growth medium on the substrate to form an array of spatially distinct, three-dimensional culture spots on the flat surface of the substrate; and placing the spotted substrate in a humidifier to grow the microbial cultures without exposing the device to additional growth media.

Other methods, compositions, plants, features, and advantages of the present disclosure will be or become apparent to one with skill in the art upon examination of the following drawings and detailed description. It is intended that all such additional compositions, methods, features, and advantages be included within this description, and be within the scope of the present disclosure.

BRIEF DESCRIPTION OF THE DRAWINGS

Further aspects of the present disclosure will be more readily appreciated upon review of the detailed description of its various embodiments, described below, when taken in conjunction with the accompanying drawings. Moreover, in the drawings, like reference numerals designate corresponding parts throughout the several views.

The patent or application file contains at least one drawing executed in color. Copies of this patent or patent application publication with color drawing(s) will be provided by the Office upon request and payment of the necessary fee.

DETAILED DESCRIPTION

Figure 1:
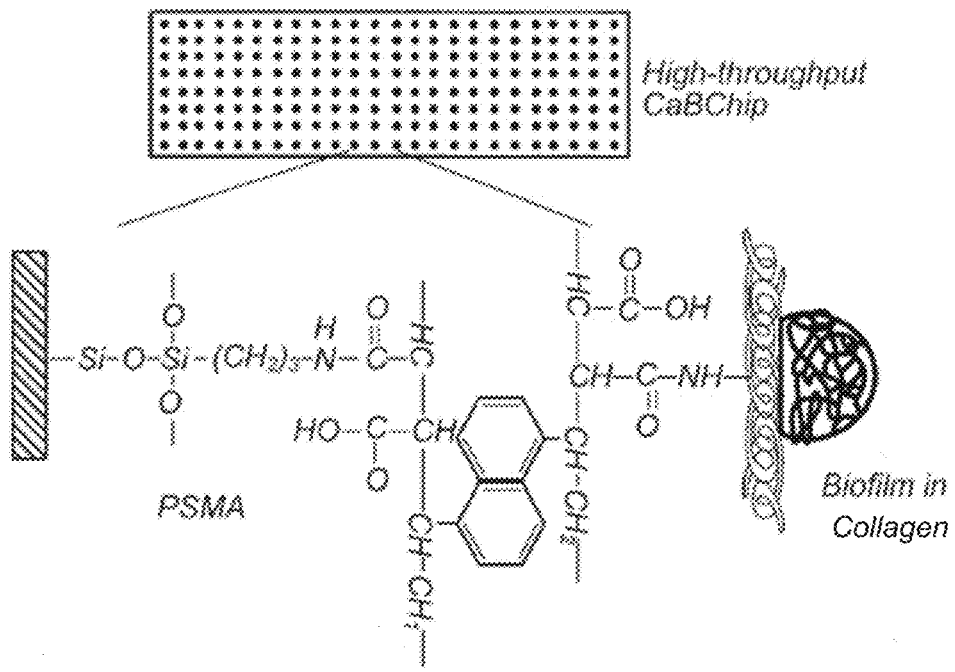
FIG. 1 depicts a schematic diagram of a biofilm encapsulated in collagen attached to a PSMA-modified substrate.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

Publications and patents cited in this specification that are incorporated by reference are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, biochemistry, molecular biology, biology, pharmacology, material science, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a cell" includes a plurality of cells. In this specification and in the embodiments that follow, reference will be made to a number of terms that shall be defined to have the following meanings unless a contrary intention is apparent. Throughout this application, the term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and "and/or."

As used in this disclosure and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") have the meaning ascribed to them in U.S. Patent law in that they are inclusive or open-ended and do not exclude additional, unrecited elements or method steps. "Consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes any prior art embodiments.

Prior to describing the various embodiments, the following definitions are provided and should be used unless otherwise indicated.

Definitions

In describing the disclosed subject matter, the following terminology will be used in accordance with the definitions set forth below.

The terms "polypeptide" and "protein" as used herein refer to a polymer of amino acids of three or more amino acids in a serial array, linked through peptide bonds. The term "polypeptide" includes proteins, protein fragments, protein analogues, oligopeptides, and the like. The term "polypeptides" contemplates polypeptides as defined above that are encoded by nucleic acids, produced through recombinant technology (isolated from an appropriate source such as a bird), or synthesized. The term "polypeptides" further contemplates polypeptides as defined above that include chemically modified amino acids or amino acids covalently or non-covalently linked to labeling ligands.

The terms "polynucleotide," "oligonucleotide," and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences) and non-coding sequences, such as, but not limited to, control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin is suggested by the terms described herein.

Use of the term "affinity" can include biological interactions and/or chemical interactions between or among a material (e.g., a compound or bio-molecule (e.g., polypeptide or polynucleotide)) and a cell. The biological interactions can include, but are not limited to, bonding or hybridization among one or more biological functional groups of the compound or cell. The chemical interaction can include, but is not limited to, bonding among one or more functional groups (e.g., organic and/or inorganic functional groups) located on the compound of cells.

An "array" includes any two-dimensional or substantially two-dimensional (as well as a three-dimensional) arrangement of spatially distinct addressable regions ("zones" and/or "spots") including one or more compounds to be tested (e.g., drugs, antibodies, antigens, other peptides, nucleic acids, microbial organisms, etc.) as well as other components, such as media, reporter compounds, and the like. The compounds/materials in each addressable region of the array can be adsorbed, physisorbed, chemisorbed, and/or covalently attached to the arrays, or maintained within the spatially distinct addressable region by a border, such as a hydrophobic border, microchannels, micropatterned borders of hydrophobic materials, and the like. The term "array" encompasses the term "microarray".

A substrate may carry one, two, four or more arrays disposed on a surface of the substrate. Depending upon the use, any or all of the arrays may be the same or different from one another and each may contain multiple spots or features. A typical array may contain one or more, including more than two, more than ten, more than one hundred, more than one thousand, more ten thousand features, or even more than one hundred thousand features, in an area of less than about 20 $cm^2$ or even less than about 10 $cm^2$ (e.g., less than about 5 $cm^2$, including less than about 1 $cm^2$ or less than about 1 $mm^2$ (e.g., about 100 $\mu m^2$, or even smaller)). For example, features may have widths (that is, diameter, for a round spot) in the range from about 10 $\mu m$ to 1.0 cm. Non-round features may have area ranges equivalent to that of circular features with the foregoing width (diameter) ranges.

One or more arrays may form part of a region of a device and/or substrate. It will also be appreciated that throughout the present application that words such as "top," "upper," and "lower" are used in a relative sense only.

An array, such as those described herein, is "addressable" when it has multiple regions of different moieties (e.g., interactive or binding sites) such that a region at a particular predetermined location (i.e., an "address") on the array can detect a particular outcome for a particular agent and/or interaction. Array features are typically, but need not be, separated by intervening spaces and/or borders.

The term "organism," "subject," or "host" refers to any living entity, including humans, mammals (e.g., cats, dogs, horses, mice, rats, pigs, hogs, cows, and other cattle), birds (e.g., chickens), and other living species that are in need of treatment. In particular, the term "host" includes humans. As used herein, the term "human host" or "human subject" is generally used to refer to human hosts. In the present disclosure the term "host" typically refers to a human host, so when used alone in the present disclosure, the word "host" refers to a human host unless the context clearly indicates the intent to indicate a non-human host.

The term "microorganism" or "microbe" as used herein refers to a small (often, but not always, microscopic) organism that is typically, but not exclusively, single cellular, and includes organisms from the kingdoms bacteria, archaea, protozoa, and fungi. The present disclosure is primarily directed to microorganisms that are pathogenic and capable of causing disease. In embodiments, microorganism includes bacteria and fungi capable of causing disease, particularly disease in humans and other mammals and animals in need of treatment.

The term "sample" can refer to a tissue sample, cell sample, a fluid sample, and the like. A sample may be taken from a host. The tissue sample can include hair (including roots), buccal swabs, blood, saliva, semen, muscle, or from any internal organs. The fluid may be, but is not limited to, urine, blood, ascites, pleural fluid, spinal fluid, semen, wound exudates, sputum, fecal matter, saliva, and the like. The body tissue can include, but is not limited to, skin, muscle, endometrial, uterine, and cervical tissue. While a sample, in the context of the present disclosure, is primarily a biological sample (e.g., from a living host) the sample may also be an environmental sample suspected of contamination by microbes, such as a water sample, food sample, soil sample, and the like. Although a liquid sample and some solid samples may be used as a test sample without modification for testing directly, if a solid sample is to be made into liquid form for testing and/or a liquid sample is to be diluted, a test sample may be made by reconstituting, dissolving, or diluting the sample in a fluid such as water, buffered saline, and the like.

The term "detectable" refers to the ability to perceive or distinguish a signal over a background signal. "Detecting" refers to the act of determining the presence of a target or the occurrence of an event by perceiving a signal that indicates the presence of a target or occurrence of an event, where the signal is capable of being perceived over a background signal.

The term "detectable signal" is a signal derived from non-invasive imaging techniques such as, but not limited to, optical imaging (including with the naked eye) (e.g., colorimetric assays), fluorescent imaging, positron emission tomography (PET), single photon emission computed tomography (SPECT), magnetic resonance imaging (MRI), computer topography (CT), ultrasound, and high-content imaging technologies, such as, but not limited to, microarray scanners and high-content microscopy. The detectable signal is detectable and distinguishable from other background signals that may be generated from the host or sample. In other words, there is a measurable and statistically significant difference (e.g., a statistically significant difference is enough of a difference to distinguish among the detectable signal and the background, such as about 0.1%, 1%, 3%, 5%, 10%, 15%, 20%, 25%, 30%, or 40% or more difference between the detectable signal and the background) between detectable signal and the background. Standards and/or calibration curves can be used to determine the relative intensity of the detectable signal and/or the background.

Discussion

In accordance with the purpose(s) of the present disclosure, as embodied and broadly described herein, embodiments of the present disclosure relate to systems, methods, and devices for growth and testing of microbial cultures, including, in some embodiments, mixed microbial cultures. Embodiments of the present disclosure include microbial testing devices, methods of making the microbial testing devices, and methods for using the microbial testing devices of the present disclosure for testing one or more test compounds for antimicrobial activity.

In the developing world infectious diseases are still the leading cause of premature death. Even in advanced societies, each year approximately 10% of all patients admitted to hospitals develop a health-care associated infection. In the U.S. nosocomial infections represent the eighth leading cause of death with a cost estimated in the billions of dollars. Other infections, such as those in the oral cavity, also add significant morbidity and costs. Antibiotic therapy still represents the primary treatment of bacterial infections, but effectiveness is impeded by the development of resistance and the emergence of new microorganisms for which effective antibiotic therapies do not exist. Development of new antibiotics does not currently represent a primary focus for most major pharmaceutical companies.

One of the major impediments to the development of newer antibiotics is the fact that classical microbiological culture techniques are incompatible with modern methodologies for drug discovery that are dominated by High Throughput Screening (HTS), and High Content Screening (HCS). HTS/HCS involves testing and analyzing the effects of libraries of thousands or even hundreds of thousands small molecules in in vitro assays to identify those bioactive molecules that affect a particular biological process/target of interest and thus may represent potential drug candidates. Thus, it is paradoxical that in this era of miniaturization and nanotechnology, culture techniques at the heart of the field of microbiology (by definition the study of things "small") are lagging behind by at least three to six orders of magnitude.

In order to address the foregoing concerns, the present disclosure provides microbial testing devices, methods of making the testing devices, and methods of testing compounds for antimicrobial activity. In embodiments, the testing devices can involve cell cultures, reagents and compounds in the nanoscale, which is amendable to high throughput screening.

The present disclosure provides high-throughput/content screening (HTS/HCS) devices (e.g., chip arrays) that allow for growth and testing of single and mixed microbial cultures. In embodiments, every spot on the device may have a single microbial species. In other embodiments, the device may include spots with different or mixed microbial species. For instance, in some embodiments, each individual "spot" on the device can include a single or mixed culture of bacterial and/or fungal organisms and/or other microbial organisms, such as, but not limited to, viral cultures. Thus, a single device can include multiple spots with a single bacterial species, a single fungal species, mixed bacterial species, mixed fungal species, mixed bacterial/fungal species, and/or other mixed microbial species. The spots on a chip may all be the same microbial species or combinations of species, there may be groups of spots with each group having different species combinations, or each spot on the device may have a different combination of species cultures. In embodiments, the cultures within the spots may form biofilms, as discussed above, offering the ability to test treatments specifically directed at counteracting and/or preventing biofilm formation.

Thus, the microbial testing devices of the present disclosure can, in embodiments, be used for HTS/HCS of antimicrobial drugs (e.g., antibacterial, antifungal, etc.). Some embodiments for HTS/HCS of antimicrobial drug candidates according to the present disclosure include a microarray-based technology. Some advantages of HTS/HCS include miniaturization and automation, which combine to cut reagent use and analysis times, minimize or eliminate labor intensive steps, and dramatically reduce assay costs. Such a chip may speed up the drug discovery process by enabling rapid, convenient and inexpensive screening of hundreds-to-thousands of compounds simultaneously. These chips may be used to identify effective drug candidates by screening of large libraries of small molecule compounds. Embodiments of the testing devices, methods of making the devices, and methods of using the devices for screening test compounds are described in additional detail below.

Microbial Testing Devices

In embodiments, the microbial testing device of the present disclosure includes spatially distinct, three-dimensional culture spots including microbial cells. As mentioned above, in embodiments, the microbial cells are selected from fungal cells, bacterial cells, or a mixed microbial culture of both fungal and bacterial cells. The present disclosure also contemplates testing devices for other microbial cells in addition to fungal and bacterial cells. In embodiments, the testing device may include only fungal culture spots, only bacterial culture spots, both fungal and bacterial spots, or spots including both fungal and bacterial cells. In some embodiments, the microbial cultures in the spots form biofilms, such as, but not limited to, fungal biofilms, bacterial biofilms, and mixed microbial (e.g., fungal and bacterial) biofilms.

In embodiments, microbial testing devices of the present disclosure include a substrate. In embodiments the substrate is flat or at least has a flat surface. Embodiments of the testing device include an adhesion material coupled to the substrate, e.g., on the flat surface of the substrate. The microbial testing device of the present disclosure includes a plurality of spatially distinct, three-dimensional culture spots on the substrate. In embodiments, the culture spots are disposed on the adhesion material on the flat surface of the substrate. The culture spots are three-dimensional and are able to substantially hold their shape after deposition. The three-dimensional aspect of the culture spots is provided, at least in part, by the inclusion of a matrix material in the culture spots. In embodiments, the culture spots include a mixture of microbial cells, a matrix material, and an amount of growth medium. The matrix material provides structural support for the culture spot, such that it retains a three-dimensional shape after being deposited on the substrate. In other words, the spot does not need to be retained by raised physical features of the substrate (as in the case of a traditional well plate). Instead, the spot retains its integrity and remains spatially distinct without needing a physical barrier provided by the substrate.

Since the spots contain microbial cells, which are more robust than other cell types (e.g., mammalian and other animal cells), the support provided by the matrix material and the nourishment provided by the initial amount of growth medium in the spot are sufficient such that the microbial cells in the culture spots are capable of remaining viable for several hours after deposition without exposing the spots to additional growth media. Unlike traditional well plates where the cells are submerged in growth/culture media, or other chip-based designs where the chip is submerged in media in order to bathe the cell spots in media, the device of the present disclosure does not need to be submerged or otherwise bathed in media, as the design of the device of the present disclosure allows the microbial cells to remain viable without exposure to additional media (e.g., media in addition to the initial amount contained in the spot at the time of deposition). In embodiments, the microbial cells in the culture spots on the device are capable of remaining viable for about 24 hours or more without addition of growth media. In embodiments, the microbial cells are capable of remaining viable for 0.5 to 48 hours without exposure to additional growth media.

In embodiments, the substrate is made of a material selected from, but not limited to, glass, natural polymer materials (e.g., paper), synthetic polymer materials, metals, metal alloys, and silicone. In embodiments, the substrate may be a combination of materials (e.g., a silicone or metal coated glass slide, etc.) In some embodiments the substrate also includes a coating that may be hydrophobic, hydrophilic, or amphiphilic depending on the needs of the application. For instance, in embodiments generally adherent cells may be used, and the choice of substrate and/or substrate coating can be chosen depending on the type/nature of the cells to be grown in the nano-scale cultures pots. Although embodiments may differ depending on the circumstances, generally, most mammalian cells, bacteria and fungi perform better on a hydrophilic surface for initial attachment to a surface, but there are exceptions. For instance, the fungi *Candida albicans* can grow on hydrophobic as well as hydrophilic surfaces, the bacteria *Staphylococcus aureus* performs best on a hydrophilic substrate, and microorganisms that grow in suspension are typically indifferent to the nature of the substrate. Although hydrophobic surfaces are typically preferred for a higher throughput use, some chemical modifications can be made to accommodate hydrophilic islands to meet any specific needs of a particular cell type.

In embodiments, the device of the present disclosure facilitates culturing microbial cells that prefer a hydrophilic surface, while the hydrophobic surrounding material (e.g., some embodiments of the matrix material, described in greater detail herein) aids in preparing high-density arrays of nano-scale cultures. In other words, the surface chemistry of the substrate, at least in part, determines the attachment of cells thereby influencing the survival and proliferation of the cell line. In some embodiments, the matrix material provides a hydrophobic surrounding that helps inhibit/prevent the hydrophilic spots from spreading or flattening, thus providing a 3D environment for the spots printed using the microarray. In addition to this, the surface chemistry of the substrate also plays a role in the formation of biofilms where the initial attachment of planktonic cells is quintessential to initiate biofilms formation. Thus, the substrate and/or substrate coating can be determined and optimized as appropriate for the cell type and whether or not planktonic or biofilms are desired. Additional examples of substrates and substrate coatings will be described below and in the examples.

In embodiments, the adhesion material includes a hydrophobic polymer, a hydrophilic polymer, or a combination of both. In embodiments the adhesion material can be, but is not limited to, one or more of the following: polystyrene-co-maleic anhydride; poly-methyl-methacrylate, polystyrene; poly-vinyl chloride; silicone, a co-polymer of two or more polymers selected from the group consisting of: a styrene, an olefin, an acrylic, an amide, an imide, a diene, an ester and an ether; and combinations thereof.

As mentioned above, the spots also contain a matrix material. In embodiments, the matrix material is admixed with the initial amount of growth medium and microbial cells prior to spotting on the substrate. In embodiments the matrix material is a gel material, such as a solgel or hydrogel that provides additional structural support/stability to the zones/spots. The matrix material provides support for the cells in the spots. In embodiments, the matrix material supports and at least partially encapsulates the cells and growth medium. In embodiments, the matrix material/medium/cell combination is spotted onto the substrate and forms self contained "islands" on the substrate. As used in the present disclosure, encapsulation indicates the cells/growth medium compositions are at least partially contained within the volume of a matrix material. Encapsulation within the volume of a matrix or adherence to the surface of the matrix can help to maintain the viability of the cells as well as retaining them on the substrate and giving them a 3D structure in/on which to grow. The support structure provided by the matrix material also provides a surface on which microbial biofilms can form.

Furthermore, the volume of a matrix material can contain more medium/cells than can be attached to a surface area equal to the footprint of a matrix spot. Depending on the matrix material, the other materials (growth/selection media, cells, etc.) may be physically encapsulated within the matrix, and/or can be adhered (such as by being covalently attached by a chemical bond) or tethered to the matrix material. In embodiments, the matrix material is at least semi-permeable. The matrix material/microbial cell/growth medium mixture can be spotted on the surface of the substrate present disclosure by various methods, such as spotting with a robotic microarray spotter, manual pipetting, and the like.

In embodiments, the matrix material can include materials such as, solgels, or a natural or synthetic hydrogels. Exemplary solgels can be substituted or unsubstituted and can include, but are not limited to: tetramethoxyorthosilicate, a methyl-trimethoxyorthosilicate, a tetraalkoxyorthosilicate, and a trialkoxyorthosilicate. In embodiments, hydrogels for the matrix material can include a protein hydrogel, polysaccharide hydrogel, peptide hydrogel, or combinations of these hydrogels or combinations of hydrogels and solgels. Hydrogels can include substituted and unsubstituted, synthetic and natural hydrogels and can include inorganic polymers, organic polymers (PEG, PLGA, PGA, polyacrylamide, agarose, PVA, gelatin-comethacrylate, etc.) and/or natural polymers (collagen, alginate, matrigel, chitosan). Hydrogels include polysaccharide gels, such as, but not limited to, an alginate, a dextran, a starch, a cellulose, a carrageenan, a poly(hyaluronic acid), a heparin, a guar, or an inulin. Other polymers include a polyvinylene, a poly (vinyl acetate), a poly(ethyl vinyl ether, a polyacrylate such as a polymethyl methacrylate, a polystyrene, a polyvinyl silicate, a polyurethane, a polyalkanoate, a poly(lactic acid), a poly(3-hydroxybutyrate), and substituted variations thereof. In embodiments, the matrix material can be selected from the group of solgels and hydrogels including: a tetramethoxyorthosilicate, a methyl-trimethoxyorthosilicate, a tetraalkoxyorthosilicate, a trialkoxyorthosilicate, a polyacrylamide, a polyacrylate, a sugar-substituted polyacrylate, polyethylene glycol (PEG), a polyvinyl alcohol, agarose, collagen, matrigel, alginate, chitosan, and other polysaccharide gels. Exemplary hydrogels include, but are not limited to, alginate, collagen, matrigel, gelatin, dextran, chitosan, poloxamer, polyethelene glycol, and combinations of these. In embodiments, the matrix material includes collagen and/or alginate. The concentration of these hydrogels can range from 0.01% to 10%; depending upon the choice and combinations of the hydrogels. In an embodiment, the matrix material includes about 0.055 to about 5% of a hydrogel. The percentage of hydrogel can be optimized for the type or types of microbial cells being grown and/or tested in the spots. Some non-limiting examples include: collagen at 0.5%, alginate at 1% and matrigel at 0.3%.

As described above, the microbial culture spots of the testing devices of the present disclosure also include an initial amount of a growth medium or combinations of growth media. This initial amount of growth medium is contained in the spot with the cells and matrix material and is sufficient to sustain growth and viability of the microbial cells in the spots for about 24 hours or more. This reduces costs and time associated with culturing the substrate in larger volumes of liquid media. The testing device of the present disclosure also provides an advantage over technologies where the substrate must be designed to be able to hold a volume of media (e.g., well plates) or must be submerged or bathed in media to sustain the cells. This is an advantage also when working with microbial cell cultures, since microbial cells (more so than mammalian and other animal cells) are capable of growing on many surfaces and, if the substrate is placed in a media bath or otherwise submerged, the cells could escape the spots and grow over other surfaces of the substrate, fouling the substrate and disrupting the array format, such that the spots may become indistinguishable. Thus, the self-contained, spatially distinct, 3D culture spots of the microbial testing device of the present disclosure provide multiple advantages over current technologies.

In embodiments, the growth media included in the culture spots on the substrate is chosen from many available growth medium and is selected based on the needs of the cells being cultured and/or the application of the testing device. The media can be a combination of growth mediums and other components and can be optimized for the cell type and application. In some exemplary embodiments, the growth medium is selected from, but not limited to, Brain Heart Infusion (BHI), Yeast Peptone Dextrose (YPD), Luria Bertani (LB), Tryptic Soy Broth (TSB), Roswell Park Memorial Institute (RPMI), and Mueller Hinton broth (MHB). The concentration of growth medium included in the spots can also be optimized for the cell type and application. In embodiments, the growth medium has a concentration of about 1× to about 10×.

The media can be optimized by choice of medium and/or inclusion of additives to control various aspects of the spots, such as pH. In embodiments, the pH of the spots is a biological pH of about 5 to about 8.5. In other embodiments, the pH of the spots is about 6.5 to about 7.5. In embodiments including microbial organisms with biological pH ranges outside of a typical biological pH, the pH of the spots can be modified accordingly. In embodiments the spotting mixture can also include a growth serum or other additives. Additional examples and description of serum and other additives to the spotting mixture are described below. Some examples of supplements or additional elements that can be added to the growth medium include, but are not limited to, serum, saliva, synthetic urine, digestive enzymes, and other compounds used to help mimic physiological conditions. Such combinations can also be used to aid in confluent culturing of microorganism and biomass optimization in nano-scale. The choice of supplements depends on the cell type(s). For instance, in vitro cultures of *Staphylococcus aureus*, *Pseudomonas aeruginosa* thrive well in the addition of human serum, mimicking physiological condition observed in patients suffering from burn and wound infections; saliva can be added to *Streptococcus gordonii* cultures to promote proliferation to physiological relevance observed in a typical oral microbiome; and *Candida albicans* grows optimally with serum-like components included in the media, such that the yeast filaments and forms biofilms.

The seeding density of the microbial cells in the spots is also optimized for growth depending on the type of microbial cell and the application of the testing device. In embodiments, each spot has a seeding density of microbial cells of about $1\times10^1$ to about $1\times10^9$ cells per ml. In some embodiments where the microbial culture spot includes at least two different microbial species (e.g., two different bacterial species, two different fungal species, a bacterial species and a fungal species, etc.) the seeding ratio of the at least two different microbial species is about 1:1 to about 1:100. In embodiments where the microbial culture spot includes more than two (e.g., three or more, four or more, etc.) different microbial species, appropriate seeding ratios can be determined based on optimizing seeding density for the various species.

In embodiments, each culture spot on the device has a volume in the nanoliter range. Due to the design of the testing device of the present disclosure and optimization of parameters such as media type and concentration, seeding density, pH, matrix material, and the like, even in the nanoliter volume, in embodiments, the microbial cultures in the spots are able to form microbial biofilms. As discussed in greater detail below, in embodiments, the microbial cultures in the spots have one or more phenotypic characteristics of a microbial culture biofilm. This allows the testing devices to be used to screen test compounds for antimicrobial activity, not just against microbial cells, but also microbial cells that have formed a biofilm, which typically provides microbial cultures with more resistance to antimicrobial drugs.

Optimizing the above parameters allows not only the propagation of single and/or mixed microbial cultures on a high-throughput platform, but also the formation of micro-scale microbial biofilms. The formation of microbial cultures with the features of biofilms on a nano-scale high-throughput device allows for faster and higher-volume testing of therapeutics for anti-microbial and anti-biofilm activity (e.g., either the prevention of biofilm formation or reduction of existing biofilms). Additional details are provided in the examples below.

The microbial microarray chips of the present disclosure provide many additional advantages over current technologies. As discussed above, unlike conventional well plate-based assays, the cells in the microarray of the present disclosure are not submerged in a pool of media. The matrix (e.g., hydrogel) encapsulating the cells is loaded with organism-specific media of engineered concentration that can keep the biofilms viable for up to about 60 h without further addition of new media. Thus, the initial media included in the "spot" with the matrix and cells is sufficient to keep the cultures viable without the need to expose the spots or submerge them in additional media. As used herein "submerge" with respect to the spots, means the spots on the substrate are placed in a bathing media, where the surface of the substrate and the spots are bathed in a culture media. Thus, the initial amount of media included in the spot, is not considered "submerging" the spot in media, nor is any subsequent spotting of test compounds or other compounds onto the existing spots, where the test composition may also include media. While the microbial cultures in the initial spot are capable of remaining viable for about 60 h without any exposure to additional media, occasionally a small amount of media is included in a composition including other compounds, such as a test compound that is spotted onto the existing spots. This does not qualify as "submerging" the spot in media in the context of the present disclosure.

The optimization of the above parameters and procedures culminated in a robust platform of individual single or mixed species nano-biofilms in each spot. Besides the advantages such as nano-scale cultures, low reagent/drug volume per assay, the ability to use these chips with a robotic-arrayer makes the assay less-laborious, and the engineered culture condition increases precision. All these factors combine to cut reagent cost, analyses time and increases the throughput per assay.

In embodiments, the testing device/system includes also a detector. A detector assays a desired feature, i.e., physical, chemical, or biological evidence of reactions, (e.g., color changes, changes in fluorescence, etc.). Examples of detectors include, but are not limited to, an electrode, an aspiration probe, a laser desorption probe, an ion beam desorption probe, a gas desorption probe, a liquid desorption. probe, a contact probe, an optical spectrometer, a microscope, an imager, a mass spectrometer, a chromatography apparatus, an electro chemical detector, a particle detector, a chemical affinity detector, a radiation detector, a magnetic resonance spectrometer, or the components to perform a cell proliferation assay, a cytotoxicity assay, an immunoassay, a binding assay, or a staining assay. Some of the components comprised by the detector, such as the various probes, are not necessarily detectors per se but function to remove a sample and direct it to another component of the detector.

In embodiments the testing devices of the present disclosure are made by obtaining a substrate as described above having a flat surface. Then a mixture including one or more types of microbial cells, a matrix material, and a growth medium are spotted on the substrate to form an array of spatially distinct, three-dimensional culture spots on the flat surface of the substrate. After spotting, the spotted substrate can be placed in a humidifier and incubated at appropriate temperature to allow the microbial cultures to grow. As discussed above, in the methods of the present disclosure, the microbial cultures are grown on the device without exposing the device to additional growth medium. Thus, in the methods of making the testing devices of the present disclosure, the microbial cells on the device are cultured without submerging the flat surface of the substrate in growth media. In other words, the substrate is neither wholly or partially submerged in growth media such that the flat surface is submerged (e.g., contained under) a volume of growth media.

As discussed above the spots can include a different microbial organism or combination of microbial organisms. In some embodiments, some (e.g., less than all) spots include different microbial organisms or combinations of organisms than some other spots. In embodiments, each spot can include a different microbial organism or combination or concentration of cells than each other spot.

In some embodiments, prior to spotting, a coating is formed on the substrate. As described above, the coating may be a hydrophobic, hydrophilic, or amphiphilic coating. In some embodiments an adhesion layer, as described above, is disposed on the flat surface of the substrate prior to spotting the matrix/cell/media mixture.

The microbial testing devices of the present disclosure can be used to screen compounds for antimicrobial activity. In embodiments, the testing devices of the present disclosure can be exposed to one or more test compounds and the culture spots can be monitored for antimicrobial activity. In some embodiments the testing devices are prepared as described above, and the spots are cultured first to grow the microbial cultures in the spots. Then the test compound(s) is spotted on the testing device (e.g., by manual spotting or by stamping, etc. as described in more detail in the description and examples below). In this manner, compounds can be tested for the ability to inhibit microbial growth (e.g., stop further growth or kill currently living microbial cells) and/or microbial biofilms (e.g., slow or reverse the growth of microbial biofilms). In other embodiments, the test compound can be spotted with or immediately after the initial culture spot, or it may be spotted just prior to addition of microbial cells to the spot; in other words it can be spotted at approximately the same time as the matrix material/microbial cell/growth medium mixture. Such embodiments can test for compounds capable of preventing growth of microbial cell cultures and/or prevention of biofilm formation.

In embodiments the test compound(s) are spotted on the device in a volume of between about 0.2 and about 5 times the volume of the matrix material for each spot. In some embodiments the test compound may include one or more test compounds in combination. In embodiments, the spots of the testing device include different microbial cultures and the test compound is the same for each spot. In other embodiments, the spots contain the same microbial cultures and the test compound, concentration of test compound, or combination of test compounds is different for each spot to screen a library of test compounds for antimicrobial activity. In yet other embodiments, some of the culture spots contain different microbial species or combinations of species, and the test compound may be different (or different concentrations and/or combinations) for each spot. The design of the testing device and the spotting of the test compounds can be tailored to the specific needs of the test. Various combinations and variations can be contemplated and implemented within the scope of the present disclosure. The testing device and methods of the present disclosure provide advantages in both flexibility convenience and speed.

Some exemplary embodiments of fungal culture testing devices, bacterial testing devices and mixed microbial testing devices are described in greater detail below and in the examples that follow.

Fungal Test Chip

The discussion above describes embodiments of microbial testing devices for various microbial organisms, alone or in combination. Embodiments of the disclosure include fungal testing devices. In one embodiment of a fungal testing device according to the present disclosure, fungal cultures are grown on a test chip. In an embodiment, *Candida albicans* (a major human fungal pathogen) is used in a *Candida albicans* Biofilm Chip. In one embodiment, a chip comprises of at least 768 spatially distinct fungal cultures, each having a volume of less than 100 nL. In an embodiment, the spatially distinct fungal cultures are disposed on a standard 1"×3" glass slide, although any size substrate may be used. Use of a glass substrate may facilitate optical testing methodologies. In an embodiment, each of the spatially distinct fungal cultures may be tested with a different compound, allowing high throughput screening of the compounds. Thus, compared to current industry standard 96-well plate, the chip embodiments will substantially cut down assay duration and cost, increase reliability, thus enabling high-throughput screening of the small molecule libraries for compounds, which can be advanced as novel antifungal agents. Table 1 depicts a comparison of the features of a 96-well plate to an embodiment of antifungal chip.

TABLE 1

Comparison of current industry standard with our screening technology

| Attribute | 96-well plate | Fungal Chip |
| --- | --- | --- |
| Volume | 100-200μ | 10-100 nl |
| Cell number (approximate) | 100,000 per well | 200-500 per spot |
| Sample size | 96 per plate | up to 2,000 per chip |
| Liquid handling | Manual pipetting | Automated dunk and rinse |
| Analysis | Colorimetric-XTT | Fluorescence w/ microarray scanner |
| Duration single run | 48 h | 18 h[a] |
| Cost per assay b | $1.32 | $0.18 |
| Estimated time to "hits"[c] | 8-12 months | 1 month |
| Estimated time from "hits to leads"[d] | 12 months | 3 months |

[a]estimated
b estimated cost per assay taking into account laboratory supplies and reagents, cost of drug, instrument use, and technician time.
[c]refers to time devoted for "primary" screening at a singled fixed concentration for a library of 20,000 compounds.
[d]refers to time for secondary screenings (dose response, screening analogues, initial PD and PK studies) for an estimated 120 hits for the identification of the most promising "leads" (1-5 compounds) to constitute candidates for drug development.

Embodiments of the present disclosure also include methods and systems for conducting high-throughput, microscale testing for antifungal agents. In use, a reaction between a drug and a spatially distinct fungal culture may be used to identify new drugs that are effective antifungal agents. For example, if fungi at a predetermined location are killed or otherwise undergo a measurable physiological or morphological change following delivery of the test compound to the location; it indicates that the compound has an effect (e.g., toxicity) on the type of fungi at the specific location. The testing device, for example, may be used to optimize a potential drug candidate or pharmacophore to improve its efficacy and/or reduce its side effects. For example, a promising antifungal compound, and various derivatives of the antifungal compound, may be applied to the different portions of the substrate. A reaction between a compound and fungi at a predetermined location can be used to identify the most promising drug candidates.

The testing device includes a substrate and a plurality of spatially distinct fungal cultures disposed on the substrate. The substrate may be formed from any material that is compatible with fungal cultures, or that may be modified to be compatible with fungal cultures. Examples of suitable substrates include, but are not limited to, tissue culture treated surfaces, a semiconductor wafer (e.g., a silicon substrate), a glass or quartz microscope slide, a metal surface, or a natural or synthetic polymeric material (e.g., paper, PDMS, PTFE, polystyrene). In an embodiment, the substrate is a flat, thin solid, such as a glass/quartz microscope slide or a silicon wafer.

In an embodiment, the substrate may be treated with an adhesion material to improve adhesion of the fungi culture to the surface of the substrate. In one embodiment, a hydrophobic polymer may be applied to the substrate (e.g., glass/quartz slide, silicon wafer, polymeric slide, etc.). For purposes of the present disclosure a polymer is considered to be hydrophobic or water-insoluble if it is "sparingly soluble" or "practically insoluble" or "insoluble" as defined by USP29 I NF 24. Examples of hydrophobic polymers include, but are not limited to, acrylic acid-based polymers, methacrylic acid based polymers, and acrylic acid-methacrylic acid based copolymers, and polyolefins (e.g., polystyrene) and modified polyolefins (e.g., polystyrene-co-maleic anhydride (PSMA). Other adhesion materials include siloxane adhesive materials. For example, amino-siloxanes (e.g., 3-aminopropyltriethoxysilane) may be used to improve adhesion of fungi to the slide. In one embodiment, a combination of a siloxane adhesive material and a hydrophobic polymer is used to treat a substrate prior to adhesion of the fungi.

Other materials that may be used to coat a substrate include, but are not limited to, proteins (collagen, poly-L-lysine), carbohydrates (hyaluronic acid), peptide tethers, and exopolysaccharide components of a biofilm matrix.

In some embodiments, the fungi may be encapsulated or adhered to the surface of a matrix material. The material of a matrix may be permeable to small molecules, including potential drug candidates. Each matrix can be the same or different material. The matrix material can be substituted or unsubstituted and includes a solgel, a hydrogel, a polyacrylamide, a polyacrylate, a polyvinyl alcohol, polyvinylene, or a polyvinyl silicate, such as a polyacrylate substituted with a sugar comprising sucrose, glucose, galactose, trehalose, mannose, or lactose. In another embodiment, the matrix material is a substituted or unsubstituted solgel.

A solgel, for example, is a tetramethoxyorthosilicate, a methyl-trimethoxyorthosilicate, a tetraalkoxyorthosilicate, or a trialkoxyorthosilicate. A hydrogel is, for example, a polyacrylamide, a polyacrylate, a sugar-substituted polyacrylate, polyethylene glycol (PEG), a polyvinyl alcohol or a natural hydrogel (collagen, matrigel). A polysaccharide gel is, for example, an alginate, a dextran, a starch, a cellulose, a carrageenan, a poly(hyaluronic acid), a heparin, a guar, or an inulin. Other polymers include a polyvinylene, a poly(vinyl acetate), a poly(ethyl vinyl ether, a polyacrylate such as a polymethyl methacrylate, a polystyrene, a polyvinyl silicate, a polyurethane, a polyalkanoate, a poly(lactic acid), a poly(3-hydroxybutyrate), or substituted variations thereof.

Encapsulation means the fungi is at least partially contained within the volume of a matrix material. Encapsulation within the volume of a matrix often maintains the activity of the fungi better than surface immobilization. Furthermore, the volume of a matrix can contain more fungi than can be attached to a surface area equal to the footprint of a matrix. Depending on the matrix material, fungi may be physically trapped or caged, and/or can be covalently attached by a chemical bond, or tethered.

Appropriate matrix materials, and encapsulation of compositions therein are described in the literature, including U.S. Pat. Nos. 5,854,030; 5,618,933, and 5,474,915, all of which are incorporated herein by reference.

Individual spatially distinct fungal cultures may be placed on the substrate using manual pipetting or a robotic microarray spotter. A robotic microarray spotter can be used in a number of ways relevant to the disclosure, including to prepare arrays of fungi cultures on a surface of the substrate. Of the many commercial spotters available, there are, for example, contact pin spotters such as the GeneTAC G3 (Genomic Solutions, Lansing, Mich.), OmniGrid (Digilab) and piezoelectric (inkjet mechanism) spotters such as the NANO-PLOTTER NP1.2® (GeSiM mbH, Grosserkmansdorf, Germany).

In use, the testing device may be used to search for new antifungal compounds. A plurality of potential antifungal compositions (testing compositions) may be applied to one or more of the fungi at predetermined locations. Interaction of the potential antifungal composition with the fungi may at the predetermined location be monitored. The compounds which exhibit the highest antifungal activities may be identified based on the locations exhibiting the most effective antifungal abilities. In one embodiment, an applied testing composition may include a hydrogel, a protein gel, a polysaccharide gel, a cellulose, a gelatin, a polystyrene, or a polyacrylamide. Examples of hydrogels that may be included in the testing composition include, but are not limited to polyvinyl alcohol, collagen, carrageenan, poly(hyaluronic acid), and inulin. In a preferred embodiment, the applied composition includes collagen. The applied composition may be added manually or using a robotic microarray spotter.

The volume of applied composition solution added can be optimized to provide efficient wetting of each matrix and enable effective partitioning of the applied composition into the matrix. For example, the volume of the applied composition solution added can be between about 0.2 and about 5 times the volume of each matrix. Alternatively, the volume of the applied composition solution added can be between about 0.5 and about 2 times the volume of each matrix.

As described above, the testing device can be monitored to detect antifungal activity (e.g., such as by detecting changes in fungal cell viability, biofilm formation, cell death, etc.) to screen for compounds that may be antifungal drug candidates. Variations to the embodiments described herein can be contemplated by those of skill in the art. Descriptions of additional, non-limiting embodiments of fungal testing devices are provided in Example 1, below.

Bacterial and Mixed Microbial Test Chips

Bacterial, Fungal and Polymicrobial Chip Design Parameters

The microbial chips of the present disclosure can be made according to the general methods described above for the fungal chip arrays and can have various elements, some of which are described in Table 2 below (all ranges and amounts are approximate). It will be understood by those of skill in the art that modifications to the parameters below are contemplated, and such modifications and alternative embodiments can be made without deviating from the purpose of the invention(s) described in the present disclosure.

TABLE 2

| Design variable | Example Embodiments/Experimental ranges |
| --- | --- |
| 1) Matrix material: Hydrogel-single/combinations of protein, polysaccharide, peptide hydrogels | 0.05%-5% of the spot volume (Alginate, collagen, matrigel, gelatin, dextran, chitosan, poloxamer, polyethelene glycol) |
| 2) Optional Adhesion layer-single/combinations of hydrophobic and hydrophilic polymers | Polystyrene-co-maleic anhydride; polymethyl-methacrylate, polystyrene; polyvinyl chloride; co-polymers of styrene, olefins, acrylics, amides, imides, dienes, esters and ethers; silicone |

TABLE 2-continued

| Design variable | Example Embodiments/Experimental ranges |
|---|---|
| 3) Seeding cell density (single/combo) | $1 \times 10^1$-$1 \times 10^9$ cells per ml |
| 4) Species seeding ratio | 1:1, 1:10, 1:100 (multiples of 2, 5 and 10) |
| 5) pH | 6.5-7.5 (depending on species) |
| 6) Growth Medium (single/combo) | BHI, YPD, LB, TSB, RPMI, MHB* |
| 7) Media concentration | 1X-10X |
| 8) Serum (10%-50%) (mixed with media or matrix material, or added separately to the spot) | Human, Bovine, Fetal calf |
| 9) Incubation Time | 1-48 h |
| 10) Temperature | 22° C.-45° C. |
| 11) Substrate | Ceramics, polymer, and glass (e.g., alumina, zirconia, calcium phosphates, bioactive glass, glass derivatives, porcelain, carbon, paper); Metals and alloys (e.g., stainless steel, alloys of chromium, nickel, titanium, gold, silver and platinum); silicones |
| 12) Species: single or mixed microbial species including fungal, bacterial, viral cultures | aerobic/anerobic/facultative microorganism, gram postive/gram negative bacteria, motile/immotile bacteria, sporulating/non-sporulating fungi, viral cultures, etc. |

*BHI, Brain Heart Infusion; YPD, Yeast Peptone Dextrose; LB, Luria Bertani; TSB, Tryptic Soy Broth; RPMI, Roswell Park Memorial Institute; MHB, Mueller Hinton broth Optimizing the above parameters allows not only the propagation of single and/or mixed microbial cultures on a high-throughput platform, but also the formation of micro/nano-scale microbial biofilms. The formation of microbial cultures with the features of biofilms on a micro/nano-scale high-throughput device, allows for faster and higher-volume testing of therapeutics for anti-microbial and anti-biofilm activity (e.g., either the prevention of biofilm formation or reduction of existing biofilms). Additional details are provided in the examples below.

The optimization of the above parameters and procedures culminated in a robust platform of individual single or mixed species nano-biofilms in each spot. Besides the advantages such as nano-scale cultures, low reagent/drug volume per assay, the ability to use these chips with a robotic-arrayer makes the assay less-laborious, and the engineered culture condition increases precision. All these factors combine to cut reagent cost, analyses time and increases the throughput per assay.

The examples below describe embodiments of high-throughput screens for single and polymicrobial cultures of fungal as well as bacterial cultures at the nano-scale level, using *Candida albicans, Staphylococcus aureus* and *Pseudomonas aeruginosa* as model organisms. Compared to the current methods for microbial growth and susceptibility testing, this technology provides advantages in terms of miniaturization and automation, which combine to cut reagent use and analysis time, minimize labor intensive steps, and dramatically reduce assay costs.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Fungal Biofilm Chip

General Discussion

The present example described an embodiment of a fungal chip including 'miniaturized' fungal biofilms (e.g., *C. albicans*) on a standard glass slide. The chip satisfies one or more of the following criteria: (i) firmly hold hundreds of spatially distinct biofilms on a single glass slide; (ii) form a 'true' biofilm, that, though small, should contain all the different morphological forms of the fungi (e.g., yeast, pseudohyphae and hyphae) growing in three dimensions; (iii) does not dry easily, allowing cells to be cultured with ease; (iv) does not detach from substrate against multiple washings; and (v) amenable for analysis with standard microarray scanner.

In the present example, cell-adhesive islands are formed on a non-adhesive, modified glass substrate so that the fungi will attach and grow on these islands, yielding a chip with defined array pattern. This was accomplished by the following steps in sequence: (i) modifying glass slides by coating with hydrophobic (or other) polymer; (ii) spotting fungi cells encapsulated (or not) in a polymerizable hydrogel or matrix dissolved in cell culture media; (iii) growth at 37 C in a humidified chamber; and (iv) monitoring the growth of cells in the spots using suitable live stain.

In this example, low density *C. albicans* biofilm chips (48 spots per slide) consisting of 500 nL spots, using a hand-held pipette were prepared. *C. albicans* strain SC5314 cell suspension in RPMI medium ($4 \times 10^6$ cells/ml final concentration) was mixed with rat tail collagen I (BD Biosciences; 2 mg/ml final concentration) in 0.01 N NaOH (Sigma). The mixture was kept in ice, and 500 nL was rapidly spotted on polystyrene coated glass slides (Ted Pella) in a regular pattern. The slides were incubated in a humidified chamber at 37° C. for 24 h. After growth, the slides were stained with fungal stain FUN1 (Molecular Probes), which stains live cells. The slides were analyzed both using a microarray scanner, and also by confocal microscopy. We were able to produce patterns that were distinct and robust, able to withstand multiple washes, and had all the morphological forms of fungi indicating that it is indeed a true biofilm.

A high-throughput product may also be prepared according to the general methods described above. A robotic microarrayer (Microsys, Digilab) was used to spot 50 nL spots of fungal cells on glass slides in a regular pattern of 48 rows×16 columns, thus producing 768 distinct biofilms on a single chip. Polystyrene-co-maleic anhydride (PSMA) and/or other coating materials, instead of polystyrene slides, may be used to improve adherence of biofilm spots. In an example, glass slides are cleaned thoroughly with 70% ethanol to remove any dust particles, acid-cleaned by sulfuric acid wash for 1 h, thoroughly washed with water, rinsed with acetone and blow-dried. The slides are spin-coated with 0.1% polystyrene-co-maleic anhydride (PSMA) in toluene, and air-dried. The basis for using PSMA functionalized slides and collagen spots is that, while the polystyrene moiety of PSMA provides a uniform hydrophobic surface, the maleic anhydride moiety covalently bonds to the amino group of lysine of collagen. Other combinations of coatings are also possible. This arrangement provides defined cell-adhesive islands on a cell non-adhesive background. Second, in order to prevent gelation of collagen during spotting, 50 nL of 0.01 N NaOH was spotted on the chip, and then acidic collagen was spotted on top resulting in in situ, on chip gelation. Culture time was 24 h, but may be reduced to 12 h or 6 h. The initial series of experiments have used *C. albicans* as a model organism to provide "proof of concept". However, this technology should also be amenable to grow of other fungal organisms (i.e. *Aspergillus fumigatus, Cryptococcus neoformans*, Zygomycetes) and also bacterial pathogens (i.e., *Staphylococcus aureus, Pseudomonas aeruginosa* and others), and may include organisms growing as biofilms and/or free living organisms.

Figure 2:
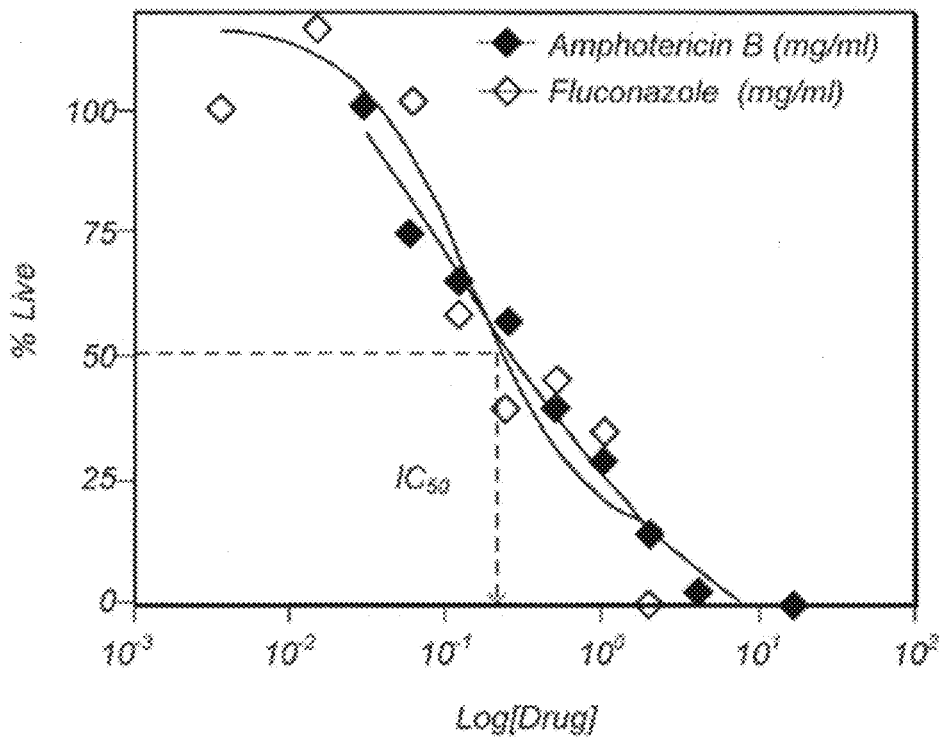
FIG. 2 depicts a graph of drug concentration vs. active fungi during testing of Amphotericin B and Fluconazole.

In one embodiment, the chip is used for high throughput screening of libraries of compounds to identify those that display antifungal activity. In one example, amphotericin B, fluconazole, and caspofungin were tested using the chip at different concentrations. After formation of the individual biofilms on the chip, the biofilms were exposed to different concentrations of these compounds for 24 hr. After this, the slides were washed by gently dunking in PBS (Sigma). The slides were then stained with FUN1, dried and read using a scanner (GenePix 4100, Molecular Devices). The $IC_{50}$ values were calculated by fitting the Hill equation to the susceptibility data using GraphPad Prism software. These results were also benchmarked by comparing with those obtained using the conventional 96-well plate employing XTT assays, with excellent results (correlation). FIG. 1 depicts a schematic diagram of a biofilm encapsulated in collagen attached to a PSMA-modified substrate. FIG. 2 depicts a graph of drug concentration vs. active fungi during testing of Amphotericin B and Fluconazole using a low density *C. albicans* biofilm chip. *C. albicans* strain SC5314, a well characterized strain from the point of view of biofilm formation, was used throughout a second study. Cells stored at −70° C. as glycerol stocks were propagated by streaking a loopful of cells onto yeast peptone dextrose (YPD) agar (1% [wt/vol] yeast extract, 2% [wt/vol] peptone, 2% [wt/vol] dextrose) and incubated overnight at 37° C. A loopful of cells from YPD agar plates were inoculated into flasks (150 ml) containing 20 ml of YPD liquid media to be grown overnight in an orbital shaker (150-180 rpm) at 30° C. Under these conditions, *C. albicans* grows as budding-yeasts.

Materials and Methods

Preparation of Functionalized Slides

Normal microscopic glass slides (1"×3") (Fisher Scientific, Waltham, Mass.) were cleaned extensively to expose the silanol groups (—SiOH) on the surface. First, the slides were placed in a removable slide rack and washed by immersing them in a staining jar containing ethanol. The slides were then wiped clean using paper towels and air-dried using nitrogen gas. Next, the slide rack containing the slides was immersed in a dish filled with concentrated sulfuric acid and incubated for an overnight treatment. Finally, these slides were subjected to sonication and washed with Milli-Q water for 30 min, following another wash in acetone. This treatment exposed the silanol groups on the glass surface.

Clean slides were then coated with 3-aminopropyltriethoxysilane (APTES) (Sigma Aldrich, St. Louis, Mo.), by immersing the slide rack in APTES for 30 min. The slides were baked in the furnace at 110° C. for 15 min. Baking allowed cross-linking of the APTES, resulting in glass slides with its surface expressing functional groups (—$NH_2$—) of APTES. Finally the slides were spin coated with 1% (wt/vol in toluene) Polystyrene-Co-Maleic Anhydride (PS-MA) (Sigma) to achieve a mono-layer of hydrophobic coating.

Optimization and printing of high density fungal cell arrays onto functionalized glass slides and subsequent biofilm development A four-factor, two-level factorial design was performed using MINITAB (Minitab Solutions Inc., State College, Pa.) and DESIGN EXPERT (Stat-Ease Inc., Minneapolis, Minn.) software to obtain optimal conditions of media concentration, seeding density, collagen concentration and PSMA coating concentration for wash-resistant biofilm growth on the CaBChip. The response (output) metrics were true biofilm yield and robust attachment, measured using microarray scanner and light microscope. For preparation of inocula for printing and biofilm formation in the CaBChip, cells harvested from overnight YPD cultures were washed twice in sterile phosphate buffered saline (PBS; 10 mM phosphate buffer, 2.7 mM potassium chloride, 137 mM sodium chloride (pH 7.4) (Sigma) by centrifugation at 3000 g. The cells were then resuspended in Reconstruction buffer (0.2N NaOH solution with 2.2% (wt/vol) Sodium Bicarbonate and 4.8% (wt/vol) HEPES). One hundred fold dilutions of the suspended cells were prepared and counted using a hemocytometer on a bright field microscope. Following count, a suspension of cells was prepared in reconstruction buffer at a cell density of $5 \times 10^7$ cells/mL, which was diluted ten times by addition of 10×RPMI-1640 supplemented with L-glutamine and buffered with morpholinepropanesulfonic acid (Angus Buffers and Chemicals, Niagara Falls, N.Y.) containing collagen (1.8 mg/ml) (Type 1 from rat tail, BD Biosciences, Bedford, Mass.), to give a final concentration of cells of $4 \times 10^6$ cells/mL. The suspension containing yeast cells, collagen and media was printed (50 nL per spot) on the functionalized PSMA-coated glass slides using a microarray spotter (Omnigrid Micro, Digilab Inc., Holliston, Mass.). Printing was carried out by non-contact deposition using conically tapered 190μ orifice ceramic tips (Digilab). The resulting spots were approximately 700μ in diameter, spaced 1.2 mm apart; spots were printed in an array of 48 rows and 16 columns. In a standard print nm, the tips were primed, rinsed in running water and vacuum dried twice after each loading and printing step. The cell suspension was kept on ice to prevent the gelation of collagen before printing and agitated gently just prior to placement on the printing robot to ensure a uniformly mixed cell suspension. A relative humidity of 97% was maintained during printing to prevent the drying of the biofilm spots. All microarray operations such as aspiration, dispensing, priming, printing and spatial distribution of array were controlled by AxSys program (Digilab). All surfaces, including the source plate station, wash and vacuum station, vacuum slide platter and printing chamber were sterilized by wiping with 70% isopropanol. In our experience, these procedures ensure that there is no detectable contamination of wells in the plates or of spots on the microarray. After printing, the slides were placed inside humidifier chambers (Arraylt Corporation, Sunnyvale, Calif.), which were placed inside a 37 C incubator over different periods of time to allow for biofilm formation.

Assessment of metabolic status of cells within biofilms

FUN 1 [2-chloro-4-(2,3-dihydro-3-methyl-(benzo-1,3-thiazol-2-yl)-methylidene)-1-phenylquinolinium iodide] (Invitrogen Corp., Carlsbad, Calif.) was used to stain and determine viability (levels of metabolic activity) of *C. albicans* cells within the biofilms formed in the chips. This membrane-permeable fluorescent dye is internalized and processed by metabolically active fungal cells, and has excitation and emission spectra that are compatible with the sets of lasers and filters installed in most microarray scanners. Briefly, the CaBChip was stained with 0.5 tM FUN 1, by simply dunking the entire CaBChip in a staining jar, and incubated in the dark at 37° C. for 30 min. Following incubation, the chip was washed three times by dunking in PBS in order to remove excess stain. The slides were then air-dried and scanned in a microarray scanner (Genepix Personal4100A, Axon Instruments, Union City, Calif.). A laser of 532 run with a PMT gain of 270 was used to read the chip and fluorescent intensity of each spot was determined using GenePix 4.1 software (Axon). Fluorescence levels from FUN 1 staining were recorded as Relative Fluorescence Units (RFU). The microarray reader converts the real fluorescence signal into an electronic signal that can be "tuned" using the gain setting or sensitivity setting, and thus RFU is an arbitrary unit. Initial experiments indicated an excellent linear correlation between number of metabolically active cells spotted on the microarray and levels of FUN 1 fluorescence.

Microscopy Techniques

Bright-field light microscopy techniques on an inverted microscope (Fisher Scientific) equipped for photography were used to routinely monitor biofilm formation, as a means of directly visualizing the overall morphology, distribution and topography of biofilms grown in the chip. The images were processed for display using Micron software (Westover Scientific, Bothell, Wash.). For scanning electron microscopy, biofilms formed in the chip were fixed with a solution of glutaraldehyde (2.5% w/v) in 0.1M sodium cacodylate buffer at pH 7.4 for 2 h at 37° C. Following fixation the biofilms were treated with a solution of osmium tetraoxide (1% w/v) in 0.1 M sodium cacodylate buffer at pH 7.4 for 2 h at room temperature. The samples were rinsed with water and soaked in a series of ethanol solutions (a step gradient of 30%, 50%, 70%, and 90% in water for 10 min per step), ending with 100% ethanol. After dehydration, the samples were dried overnight in a vacuum dryer and subsequently coated with a 60:40 gold-palladium alloy; approximately 10 nm thick using a Cressington Sputter coater for a duration of 30 sec. Scanning electron microscopy was performed using a Zeiss EVO 40 electron microscope (Carl Zeiss, Thronwood, N.Y.). Confocal Scanning Laser Microscopy (CSLM) of FUN 1 stained biofilms to visualize three dimensional patterns and determine the architecture of the biofilms grown in the chip. CSLM was performed with a Zeiss LSM 510 confocal microscope (Carl Zeiss), using a rhodamine/fluorescein isothlocyanate protocol with excitation at 488 run (argon ion laser). Images of sections in the xy plane were taken along the z axis, acquired by the resident software and processed using AutoQuant (Media Cybernetics, Bethesda, Md.) and IMARIS 6.4 (Bitplane, St. Paul, Minn.).

Susceptibility Testing of Cells Within Preformed *C. Albicans* Biofilms in CaBChip Against Antifungal Agents Susceptibility testing of cells within *C. albicans* biofilms in CaBChip was performed against clinically used antifungal agents amphotericin B and fluconazole. Amphotericin B was obtained as a powder from Sigma (St. Louis, Mo.). A stock solution of Amphotericin B (1.6 mg/ml) was prepared in DMSO and stored at −20° C. until used. Fluconazole was obtained as injection from Sicor Pharmaceuticals, Inc. (Irvine, Calif.). A stock solution of Fluconazole in 0.9% Sodium Chloride solution, available as injection was stored at 4° C. until used. Subsequent dilutions of the antifungals were made in RPMI-1640 media supplemented with L-glutamine and buffered with MOPS. On top of the biofilms formed after 24 h, drugs of desired concentration of equal spot volume (50 nL), in two-fold dilutions were spotted using the robotic microarrayer.

The CaBChip(-s) containing drugs were then incubated in a humidified chamber for an additional 24 h, after which the slides were washed by gently dunking them in PBS. Eight different concentrations of the drugs in six replicates, with appropriate positive (no drug) and negative (dead cells) controls were tested on a single CaBChip. Multiple (at least two) chips were processed in parallel. Thus, depending upon the efficacy of the drug and its dose, each spot had different fluorescence levels and by quantifying these values at each spot, susceptibility profiles for each compound were determined. The fluorescence intensity of the control and dead (killed with sodium hypochlorite for 20 min) biofilms were arbitrarily set at 100% and 0% respectively, and the inhibitory effects of compounds were determined by the reduction in fluorescence intensity in relation to the controls, as measured in the microarray scanner. Data was calculated and expressed as percent biofilm inhibition relative to the average of the control wells. SMIC50 and SMIC80 values for each antifungal were determined as before. The calculated IC50 (Inhibitory Concentration of drugs required to reduce the fluorescence intensity by half, compared to live -controls) values were determined by fitting the constant slope Hill equation (an equation determining the non-linear drug dose-response relationship) using GraphPad Prism software (La Jolla, Calif.). For comparison purposes, antifungal susceptibility testing was also performed using the 96-well microtiter plate model of C. albicans biofilm formation previously developed by our group, that uses the colorimetric (2,3-bis(2-methoxy-4-nitro-5-sulfo-phenyl)-2H-tetrazolium-5-carboxanilide) (XTT) assay as a measure of viability of cells within biofilms.

Results and Discussion

Traditionally, most models for the formation of C. albicans biofilms are cumbersome, requiring expert handling, large volumes, long processing times and the use of specialized equipment not generally available in a regular microbiology laboratory. Frequently biofilms are grown on catheter disks or sheets placed inside a fermentor or a bioreactor under either static or dynamic flow conditions. These culture techniques are slow, complex and demanding, and were mitigated to a great extent by the development of a 96-well microtiter plate model for the formation of C. albicans biofilms. In this model, fungal biofilms are formed on the bottom of the wells of microtiter plates, and the ability of metabolically active sessile cells to reduce a tetrazolium salt (XTT) to water-soluble orange formazan compounds, the intensity of which can then be determined using a microtiter-plate reader, is used as a semi-quantitative measurement of biofilm formation. This model was also adapted for antifungal susceptibility testing of cells within the biofilms. However, in this era dominated by high throughput demands and "hunger for speed", the multiwell plate format still suffers from several limitations, most importantly inefficient liquid handling and removal without disturbing the biofilms, which severely limits the automation of this process. Other disadvantages of 96-well microtiter plate model include the need for relatively larger volume of reagents (thereby increasing costs) as well as incompatibility with high content experimentation and image analysis. A microarray format/platform ameliorates all these issues, thus allowing for truly high-throughput applications. Though the microarrays have been used to great benefit in the fields of genomics and proteomics, comparatively little effort has been directed toward using cellular microarrays, particularly in the case of pathogenic microorganisms.

Design and Fabrication of the Candida Albicans Biofilm Chip (CaBChip)

An objective of the present example was to develop a high density microarray of spatially addressable three-dimensional biofilms of C. albicans, which should satisfy the following criteria: (i) firmly hold hundreds of spatially distinct biofilms on a single glass slide; (ii) forms a 'true' biofilm, and though small, displays phenotypic properties comparable to those of regularly-grown biofilms (e.g., growth, morphological and architectural characteristics and increased drug resistance); (iii) does not dry easily so that the cells may be cultured for prolonged periods of time; (iv) attaches robustly to the substrate and does not detach against multiple washings; and (v) fully compatible for analysis with a standard microarray scanner. We first performed a series of proof-of-concept experiments, mostly using manual pipetting prototypes, to check multiple parameters of biofilm formation, including those related to surface chemistry, matrix encapsulation, growth media and inocula preparation.

The first criteria in the present example was that of a hydrophobic surface, allowing for discrete, independent liquid spots of small volume (in the nanoliters range) to be deposited on the surface of the microscope slide. Thus, the borosilicate (glass) slides were first pre-treated with 3-aminopropyltriethoxysilane (APTES), followed by coating with polystyrene-co-maleic anhydride (PSMA). The styrene-co-maleic anhydride molecules zip together forming a mono-layer made of two molecules in cross section, thus enhancing the hydrophobicity of the substrate. The PSMA also provides sufficient functionality for subsequent covalent binding to an encapsulating matrix such as collagen. The use of an encapsulating matrix was implemented after initial experiments indicated that, in order to form robust (capable of withstanding the multiple washing steps) C. albicans biofilms on the microscope slides, additional support and encapsulation was desirable. The use of collagen as the matrix of choice was mostly due to its optimal and easily controllable gelation characteristics, covalent binding to the functionalized surface, and the fact that it represents a biological substrate that mimics the tissue extracellular matrix in vivo. Next, using a two-level factorial design, optimal operating parameters were developed: namely, concentrations of collagen, PSMA, C. albicans seeding density and growth media, that maximized the biofilm yield on spots that are stably attached to the substrate. Observations suggested that (i) high collagen concentration did not favor filamentation, and cells remained in planktonic form; and, on the other hand, low collagen concentration did not favor robust attachment of spots; (ii) excessively rich media resulted in hyper-filamentation forming a pseudo-biofilm, and poor media did not promote sufficient cell growth; (iii) high seeding density did not favor biofilm formation; and (iv) high PSMA coating concentration promoted stable attachment of spots. Hence, it was determined that for the present example, a collagen concentration of 1.8 mg/ml with cell seeding density $4 \times 10^6$ cells/ml in a 4×RPMI media printed on 0.1% PSMA-coated surfaces will yield an optimal biofilm chip.

Finally, the high density arrays were printed using a robotic microarrayer. A total of 768 spots of 50 nL each, containing a suspension of C. albicans yeast cells in collagen and microbiological media were spotted on the substrate. This resulted in hemispherical spots that were about 700μ in diameter, with a spot-to-spot distance of 1.2 mm. After initial printing, the slides were simply incubated under inside humidifying chambers (to prevent drying) at 37° C. to allow for biofilm development. No additional media was added to the biofilm chip after initial spotting, which is in stark contrast with most models in which biofilms are submerged in large volumes of media. The extent of biofilm formation was assessed using FUN 1, a simple and sensitive assay for fluorescent staining of metabolically active fungal cells, which is fully compatible with standard microarray scanners.

Growth Characteristics and Morphological and Architectural Features of C. Albicans Biofilms in the CaBChip By using conventional methods for C. albicans biofilm formation, it is well established that the process of biofilm development occurs through different phases, including initial adherence of cells to a substrate, followed by growth and proliferation (which in the case of C. albicans is intimately associated with filamentation), and a final maturation phase that also includes accumulation of the extracellular matrix. To further establish the kinetics of biofilm formation in the chip format, the growth of viable cells in collagen gel spots on the CaBChip were monitored over time using both microscopy and FUN 1 staining. This fluorescent dye is processed biochemically in the cytoplasm of living cells, forming cylindrical intravacuolar structures and rendering a fluorescent signal that can be read with a regular microarray reader using the appropriate excitation and emission filters. Similar to regular biofilms, direct bright-field microscopic observations revealed that *C. albicans* biofilms formed in the CaBChip are composed of yeast, pseudohyphae and hyphae. The results from these series of experiments indicated that, after a somewhat extended lag time of about 4 hours, cells grew rapidly and developed biofilms with maximum readings observed at approximately 12-18 h for what seem to be fully developed, complex biofilms. After 18 h, there was a reduction in the metabolic activity of biofilm cells, thus indicating that biofilms had reached maturity. Thus, it would seem that, compared to other standard methods in which formation of mature biofilms typically occurs over 24-48 h and beyond, the process of biofilm development and maturation is somewhat accelerated in the chip, most likely due to the sub-microliter volume range, which in turn may result in faster nutrient depletion and accumulation of metabolic waste.

In order to further ascertain the morphological and architectural characteristics of biofilms in the CaBChip, SEM and CSLM were used. SEM provides a visual description of the biofilms at higher magnification. At the highest magnification it was seen that the fungal hyphae are embedded within the matrix of collagen fibers, which are approximately 2μ and 100 nm in diameter, respectively. Contrary to SEM, the non-destructive nature of CSLM allows for the visualization of biofilms in its native state. Results of FUN 1-stained biofilms using CSLM indicate that the biofilms formed in the CaBChip show spatial heterogeneity, with regions of metabolically active cells interspersed within the extracellular matrix, which is not stained by the metabolic dye. The thickness of the biofilm was estimated to be approximately 50μ. Thus, from the point of view of their morphological, structural and architectural properties and despite several thousand-fold miniaturization, the nano-scale biofilms formed on the CaBChip display phenotypic characteristics that are comparable to *C. albicans* biofilms formed using standard methodologies.

Validation of the CaBChip for High-Throughput Analyses and Antifungal Susceptibility Testing An important aspect of a high density array is the ability to make multiple measurements at a single time. Thus, an objective was to demonstrate that all *C. albicans* biofilms formed in a same CaBChip could be formed sufficiently equivalent to each other, for its future use in large scale high throughput/high content screening applications. To this end, the viability stain FUN 1 and operating parameters of the microarray scanner were optimized such that the fluorescence intensity correlated linearly with cell number over the range of interest. It was also noted that fluorescent intensities from spots that are seeded at same initial cell density were statistically indistinguishable indicating uniform distribution of biofilms at different locations on the CaBChip. This demonstrates that the CaBChip is a valid microarray-based platform for high-throughput screening techniques, including drug discovery or the screening of large collections of mutant strains, which will allow for the genetic dissection of the biofilm developmental process.

From a clinical perspective, one of the main negative consequences of biofilm formation is the high levels of antifungal drug resistance against most clinically used antifungal agents exhibited by *C. albicans* cells within biofilms. This is one of the major contributors to the unacceptably high morbidity and mortality rates associated with candidiasis, despite of $3 billion per year spent on antifungal medications in the US alone. Thus, there is an urgent need for the development of new and improved antifungal therapies, and the process of biofilm formation represents a very attractive target. In order to ascertain the functionality of CaBChip in determining the susceptibility profiles of antifungal drugs against pre-formed biofilms, antifungal susceptibility testing was carried out for 24 h *C. albicans* biofilms grown on CaBChip against fluconazole and amphotericin B. Using the robotic arrayer, drug concentrations of double-increments were spotted on top of the mature pre-formed biofilms on CaBChip and incubated for an additional 24 h period, after which time FUN 1 was added. The fluorescence intensity of control (no drug) and sodium hypochlorite-treated dead biofilms were arbitrarily set at 100% and 0% respectively, and the inhibitory effects of the antifungal agents were determined by the reduction in fluorescence intensity in comparison to the controls. As in the case of biofilms formed using regular methods (i.e. 96 well microtiter plate model), the biofilms formed on CaBChip were observed to be intrinsically resistant to fluconazole with $SMIC_{50}$ and $SMIC_{80}$ values of >1,024 μg/ml. The calculated $IC_{50}$ for fluconazole was >1,024 μg/ml. Also similar to regularly formed *C. albicans* biofilms, amphotericin B was effective against biofilms formed on CaBChip, but only at relatively high concentrations. The calculated $IC_{50}$ for amphotericin B was 0.27±0.04 μg/ml, and the $SMIC_{50}$ and $SMIC_{80}$ values were 0.5 and 1 μg/ml, respectively. These results are consistent with those previously reported for biofilms formed using conventional techniques and once again further corroborate that, despite a near 2,000-fold miniaturization (compared to biofilms formed using the conventional 96-well microtiter plate model), the nanoscale biofilms on the CaBChip display phenotypic properties, including high levels of antifungal drug resistance, that are similar to those formed using standard techniques.

In summary, the present example demonstrates the successfully development of a cell-based, high density microarray, CaBChip, for the formation of *C. albicans* nano-biofilms. Besides providing cell-specific islands on the substrate, the hydrophobic coating on the CaBChip allows for an increased number of spots that could be printed in a microscope slide. In addition, the choice of a suitable hydrogel, as a "matrix" that encapsulates the individual biofilms and enhances the robustness of the chip. Maintaining the integrity of the gel and controlling the adhesion of the matrix onto the substrate affect the robustness and performance of the chip. Despite nanoliter volume, the resulting biofilms demonstrate phenotypic characteristics that are consistent with the *C. albicans* biofilm mode of growth. The technology is flexible and we are currently adapting it to other fungal and bacterial organisms. Thus, the CaBChip is truly high-throughput: it employs nano-scale cultures, enables rapid and easy handling, is amenable to automation, and is fully compatible with standard microarray technology and equipment. In the format described in the present example, a single CaBChip replaces up to eight 96-well plates, and multiple chips can be printed and processed simultaneously. By virtue of its miniaturization and automation, the use of this technology platform minimizes manual labor, cuts reagents use and drastically reduces assay costs. By enabling rapid, convenient and inexpensive screening of hundreds-to-thousands of compounds simultaneously, the use of CaBChip in high-content screening applications has the potential for changing the face of the antifungal drug discovery process.

Example 2

Bacterial Biofilm Chip

As discussed above, bacterial organisms represent etiological agents responsible for the majority of human infections. For example, population-based surveillance studies indicate that each year approximately 5% to 10% of all patients admitted to one of 7,000 acute care hospitals in the U.S will develop a health-care associated infection [1,2]. Under the assumption that 40 million hospital admissions occur each year, these percentages translate into a total of 2-4 million nosocomial infections. These infections add incremental morbidity, mortality, length of stay and economic cost compared to those expected from the underlying diseases alone. Gram-positive and gram-negative microorganisms account for 64% and 27% of cases, respectively, of all bacterial nosocomial infections. In addition, many different bacteria have been implicated in endocarditis, burn and wound infections; which are among the most common bacterial infections in humans and also cause significant morbidity. Bacterial organisms are increasingly resistant to currently used antibiotics, and pipelines for new antibiotics are drying up. Thus far, nano-scale HTS/HCS technologies have not been successfully implemented for antimicrobial testing. To conquer this formidable challenge, and using the pathogenic opportunistic bacteria *Staphylococcus aureus* and *Pseudomonas aeruginosa*, this example provides a high-density technique for microbial culture at the nanoscale level.

The high-throughput screening devices/chips of the present disclosure provide the ability to test multiple bacterial species on a single device. For the testing devices of the present example, the growth conditions, namely, pH, temperature, hydrogel matrix-type, strength and concentration, media-type, concentration and combinations; and seeding cell concentrations were successfully optimized for maximal biofilm yield of the microbial organism(s) (Table 3).

Materials, Methods & Results

Culture conditions. Bacterial cells, stored at −80° C. in glycerol stock, were cultured on blood-agar plates and incubated at 37° C. for 24 h. Bacterial cells were subcultured in liquid tryptic-soy broth media and grown in an orbital shaker at 37° C. for 24 h.

Fabrication of microarray slides. Borosilicate glass slides were rinsed in a staining jar with 99% ethanol and treated with concentrated sulfuric acid for 12 h. The slides were air-dried using a stream of nitrogen gas, rinsed with Milli-Q water, and baked at 80° C. for 30 min. The slides were coated with 2.5% 3-aminopropyltriethoxysilane (APTES) (wt/vol in toluene) and baked at 120° C. for 15 min, generating a layer of cross-linked APTES. Finally, the slides were spin coated with 0.3% (wt/vol in toluene) poly(styrene-comaleic anhydride) (PSMA) at 3,000 rpm for 30 s. Using a microarray spotter, a mixture of 30nL of 0.01% poly-l-lysine and 0.1 M barium chloride were printed on PSMA coated slides in an array of 1200 spots in 60 rows and 20 columns. The slides were stored at 4° C. until further use.

Factorial design. To fabricate a robust nano-biofilm microarray that would support the growth of true biofilms, the experimental conditions were optimized by a two-level four-factor experimental design model (Minitab and Design of Experiment [DoE] software). The effect of experimental variables, including cell-seeding density, concentration media, PS-MA coating, and alginate matrix, was evaluated for two qualitative outcomes, namely, morphological characteristics of the biofilm (and its yield) and robust attachment of spots on slides. Thus, the cell-seeding density, media, and alginate matrix composition were established by the results of the DoE simulation.

Microarray printing. For preparation of inocula for printing and nano-biofilm formation in the microarray, cells harvested from overnight bacterial cultures were washed twice and resuspended in sterile phosphate-buffered saline (PBS). The cell suspension of *S. aureus* was adjusted to a density of $1.5 \times 10^8$ cells/ml in 3×BHI (Brain-Heart Infusion) media supplemented with 10% human serum and then added to alginate to give a final concentration of $5 \times 10^7$ cells/ml in 1.5% alginate. Similarly in the case of mono-culture bacterial biofilms of *P. aeruginosa*, the cell suspension of *P. aeruginosa* was adjusted to a density of $1.5 \times 10^8$ cells/ml in 2×YPD (Yeast Peptone Dextrose) media supplemented with 10% human serum and then added to alginate to give a final concentration of $5 \times 10^7$ cells/ml in 1.5% alginate The suspension containing bacterial cells, alginate and media was printed (30 nl per spot) on the Poly-L-Lysine-Barium chloride spots of the functionalized PSMA-coated glass slides using a noncontact microarray spotter (Omnigrid Micro, Digilab Inc., Holliston, Mass.) with conically tapered 100-µlong orifice ceramic tips. An array of 60 rows and 20 columns was printed at room temperature with relative humidity of 100%. In a standard print run, the tips were primed, rinsed in running water, and vacuum dried twice after each sample-loading and printing step. The slides were then placed in a humidified hybridization cassette (Arrayit, Sunnyvale, Calif.) to prevent evaporation of spots and incubated at 37° C. All microarrayer functions such as sample loading, priming, printing, and spatial distribution of the array were controlled by AxSys programming (Digilab).

The growth conditions, namely, pH, temperature, matrix, media, cell-seeding density and staining can be optimized as appropriate for different embodiments to obtain favorable growth conditions for embodiments of the polymicrobial chip (sample ranges for various embodiments are described in Table 3).

TABLE 3

Experiments chip design for single sp. bacterial nano-biofilm chip [*S. aureus*/*P. aeruginosa* biofilm].
All amounts and ranges are approximate.

| Design variable | Experimental range |
| --- | --- |
| Alginate | 0.35% |
| Seeding cell density | $1 \times 10^4$-$1 \times 10^8$ cells per ml |
| pH | 7.0 |
| Medium | BHI or YPD |
| Media concentration | 2-3X |
| Serum (10%-50%) | Human |
| Time | 6-48 h |

*BHI, Brain Heart Infusion; YPD, Yeast Peptone Dextrose

Viability assay. The viability of the bacterial nano-biofilms was determined based on their metabolic activity, using 5 µM of SYTO-9 and 10 µM Propidium Iodide (PI) dye. Upon staining, the SYTO-9 fluorescent dye is internalized and processed by all bacterial cells however only the dead cells with compromised membrane-integrity internalize propidium iodide dye. The excitation/emission spectra of SYTO-9 (480/500 nm) and PI (490/635 nm), are compatible with the sets of lasers and filters installed in most microarray scanners (488 nm for excitation and 532/635 nm for emission). The nano-biofilms were stained by simply immersing the entire microarray slide in a staining jar, and incubated in the dark at 37° C. for 30 min.

Figure 3:
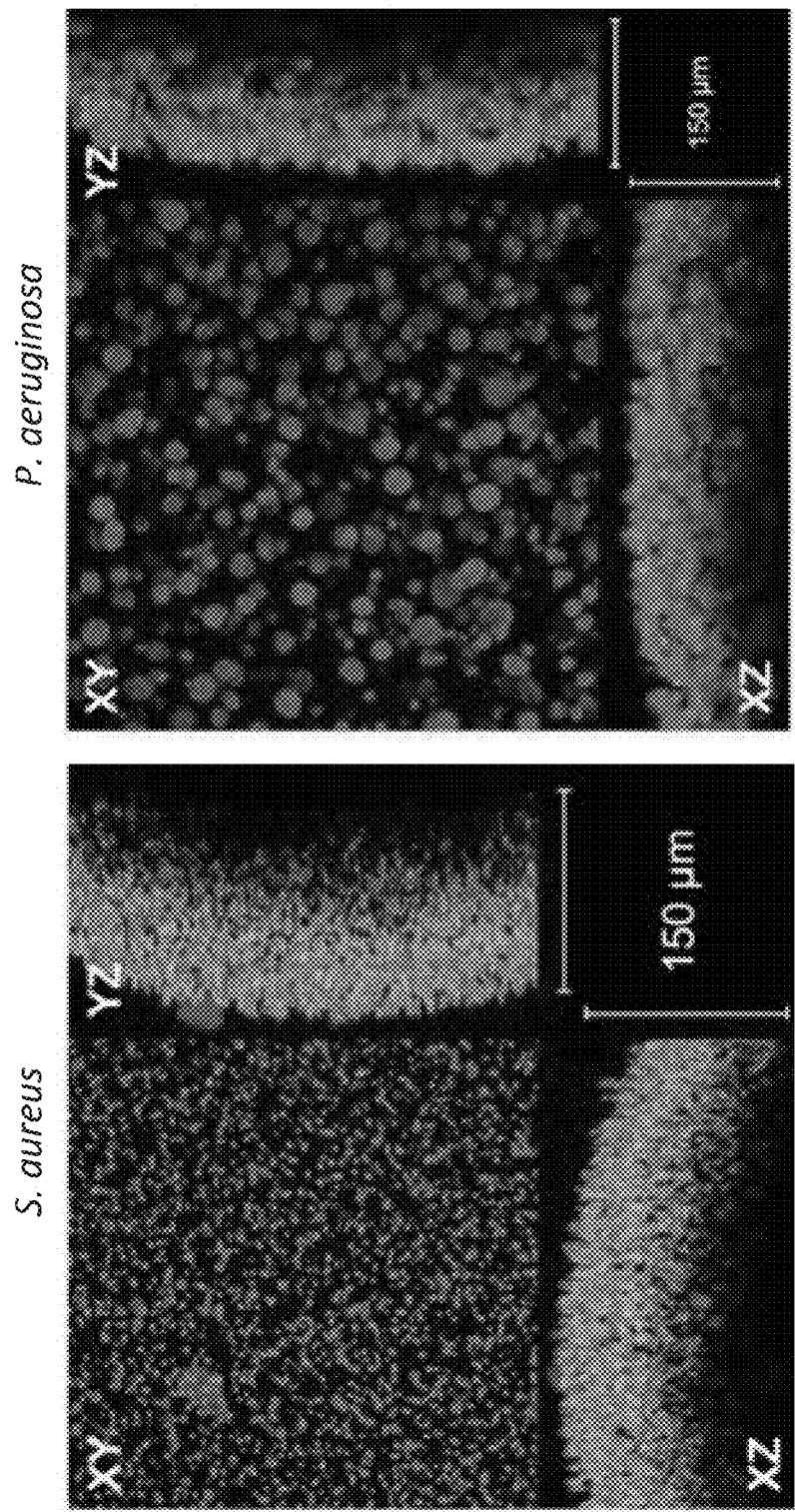
FIG. 3 represents confocal microscopy images of *S. aureus* and *P. aeruginosa* (yellow and red cells) nano-biofilm cultured on an embodiment of chip of the present disclosure after 16 h incubation.
Figure 4:
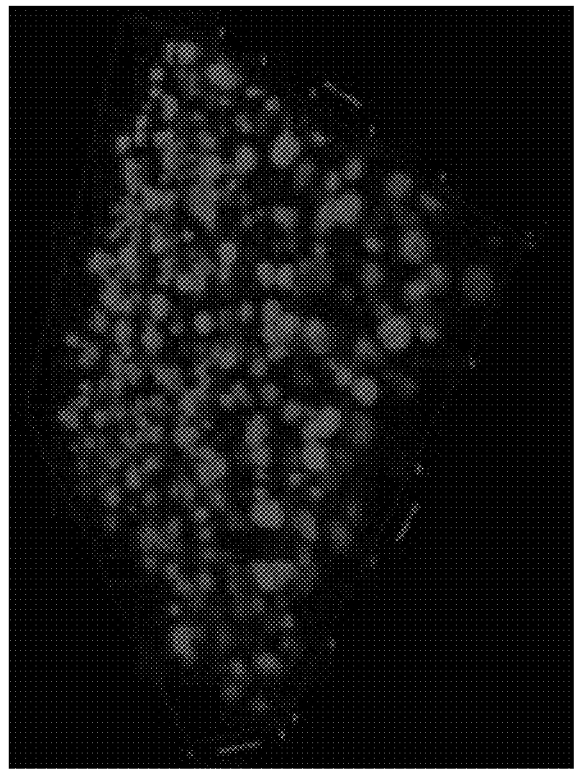
FIG. 4 shows confocal microscopy images illustrating exopolymeric material produced by *S. aureus* and *P. aeruginosa* (red color) nano-biofilm cultured on a chip after 16 h incubation.
Figure 4:
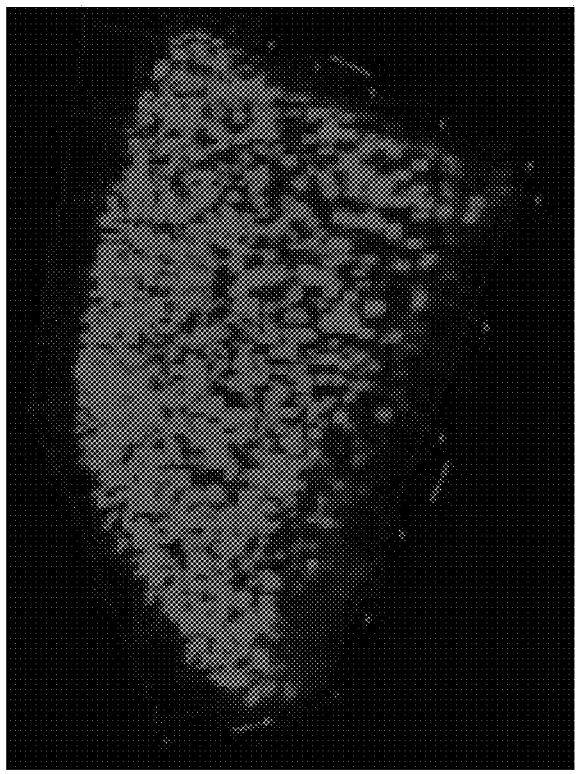

In the present example, the biofilms on the chips were stained using BacLight—an assay kit to measure bacteria viability and SYPRO film tracer to demonstrate the metabolically active cells embedded in an exopolymeric matrix material. After staining, the slides were incubated for about 30 min at 37° C. Following incubation, the microarray slide was washed three times by immersion in phosphate-buffered saline (PBS) to remove excess stain, air-dried, and scanned in a microarray scanner (GenePix Personal 4100A; Axon Instruments, Union City, Calif.). Images were analyzed with GenePix Pro V7 (Axon Instruments, Union City, Calif.). In FIGS. 3 and 4, the confocal microcopy images show nano-scale mono-culture biofilms of S. aureus and P. aeruginosa, respectively, embedded in the exo-polymeric matrix, inherently produced by the biofilms (FIG. 4).

Figure 5:
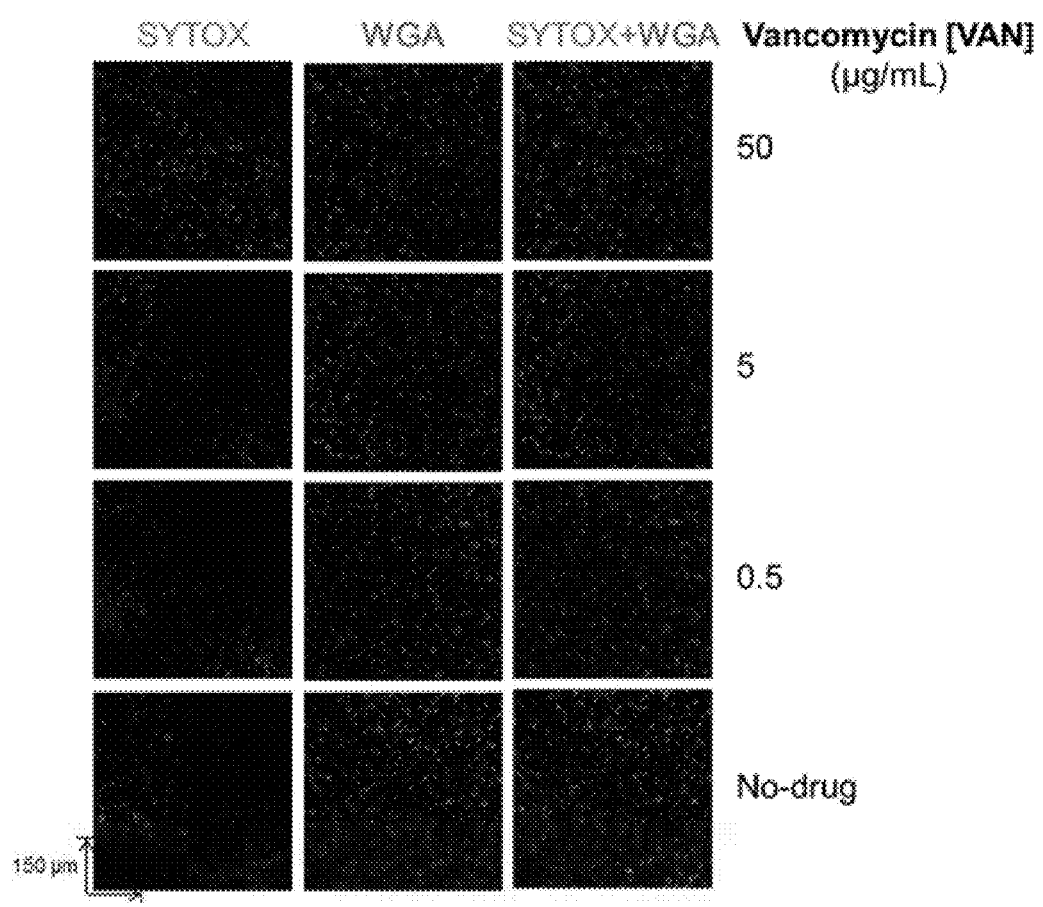
FIG. 5 shows microscopy images illustrating drug-susceptibility of *S. aureus* nano-biofilms against different dilutions of vancomycin. SYTOX (green color-left panel) stains the nucleic acid and chromosome of dead bacteria. Wheat germ agglutinin (WGA) binds to the sialic acid and N-acetyl glucose amine of gram positive bacteria; differentially staining the gram-positive bacteria (red color-middle panel) (right-hand panel shows both SYTOX and WGA (green and red)).
Figure 6:
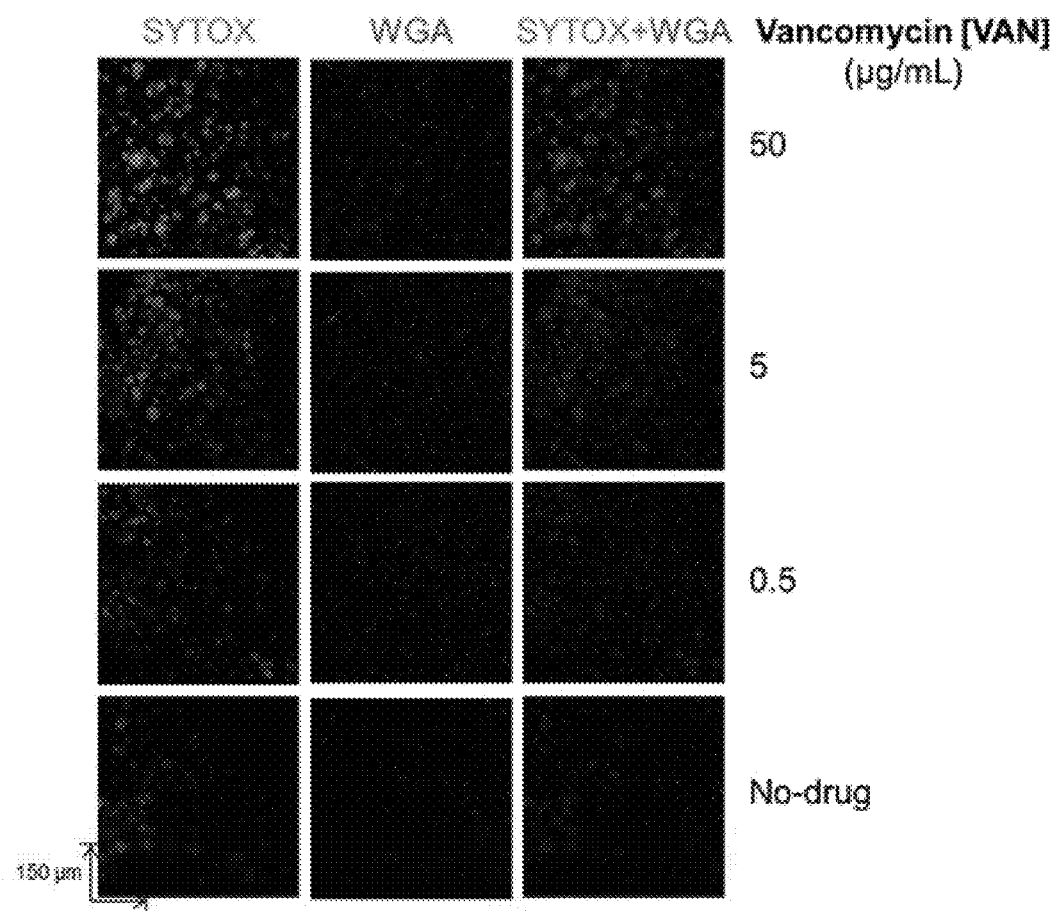
FIG. 6 represents microscopy images illustrating drug-susceptibility of *P. aeruginosa* nano-biofilm against different dilutions of vancomycin. SYTOX (green color-left panel) stains the nucleic acid and chromosome of dead bacteria. Wheat germ agglutinin (WGA) does not bind to gram-negative bacteria (red color-middle panel) (right-hand panel shows a combination image of SYTOX and WGA).

The bacterial cultures were tested with antibacterial drugs and stained with viability dye/assay-kits to measure for viable population after drug treatment. For proof of concept, the susceptibility profile of these nano-biofilms was demonstrated against different concentrations of vancomycin. The biofilms were stained with SYTOX and wheat germ agglutinin (WGA) to probe for dead cells and gram-positive bacteria, respectively. Following incubation with drug, the microarray slide was washed three times by immersion in phosphate-buffered saline (PBS) to remove excess stain, air-dried, and scanned in a microarray scanner (GenePix Personal 4100A; Axon Instruments, Union City, Calif.). Images were analyzed with GenePix Pro V7 (Axon Instruments, Union City, Calif.). Microscopy images demonstrating drug-susceptibility of S. aureus and P. aeruginosa against different dilutions of vancomycin are shown in FIGS. 5 and 6, respectively.

Example 3

Polymicrobial Bacterial Biofilm Chip

Patients with significant thermal injury (>75% total body surface area) are predisposed to infection due to immunosuppression induced at the site of injury [9]. It is estimated that the high mortality rate in burn wound injuries is due to sepsis; imparting secondary complications due to nosocomial infections, pneumonia and other biomedical-assist device infection [10]. The polymicrobial nature of these infections is recognized with increasing frequency in burn wound injuries where the microorganisms adapt to biofilm mode of growth to favor survival [8,30]. Gram-positive bacteria such as Staphylococcus can survive the thermal insult and serves as the first set of microorganisms to colonize the wound (within 48 h) [31]. Eventually, these wounds get co-colonized with other gram-positive, gram-negative bacteria and yeasts derived from the inherent microbial flora of the patient or the surrounding environment [32,33]. Among many polymicrobial communities, the interaction between S. aureus and P. aeruginosa has been reported as the most predominant colonization in burn wound injuries.

Thus, the present example describes a cellular array containing mixed biofilms of S. aureus and P. aeruginosa (e.g., two species on the same "spot" on the array) to aid in the high-throughput screening of antimicrobials that inhibit polymicrobial biofilms. The growth conditions, namely, pH, temperature, matrix, media, cell-seeding density and staining were optimized as described below to obtain favorable growth conditions for the polymicrobial chip (Table 4). Materials and methods not described herein are as set forth in Example 2.

TABLE 4

Experimental parameters and results for polymicrobial nano-biofilm chip [S. aureus-P. aeruginosa biofilm]. All amounts and ranges are approximate.

| Design variable | Experimental range |
| --- | --- |
| Alginate | 0.3%-0.45% |
| Seeding cell density (Bacteria) | $1 \times 10^4$-$1 \times 10^8$ cells per ml |
| Seeding ratio | 1:1 |
| pH | 7.0 |
| Medium | YPD, BHI, TSB |
| Media concentration | 2X YPD + 3X BHI (or) 1X YPD + 1X TSB + 2X BHI, |
| Serum (10-50%) | Human |
| Time | 6-48 h |

*BHI, Brain Heart Infusion; YPD, Yeast Peptone Dextrose; TSB, Tryptic Soy Broth

Figure 7:
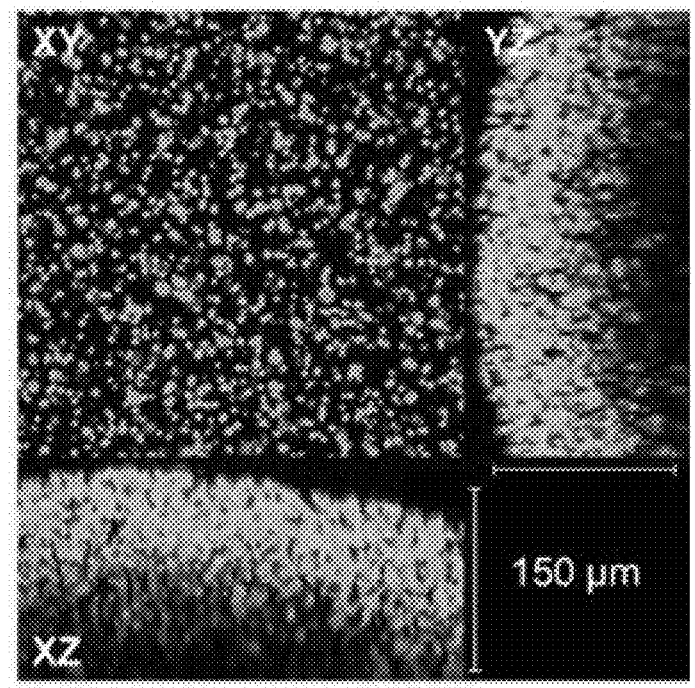
FIG. 7 is a confocal microscopy image of *S. aureus-P. aeruginosa* (yellow and red cells; intermixed) mixed nano-biofilm cultured on a chip after 16 h incubation.
Figure 8:
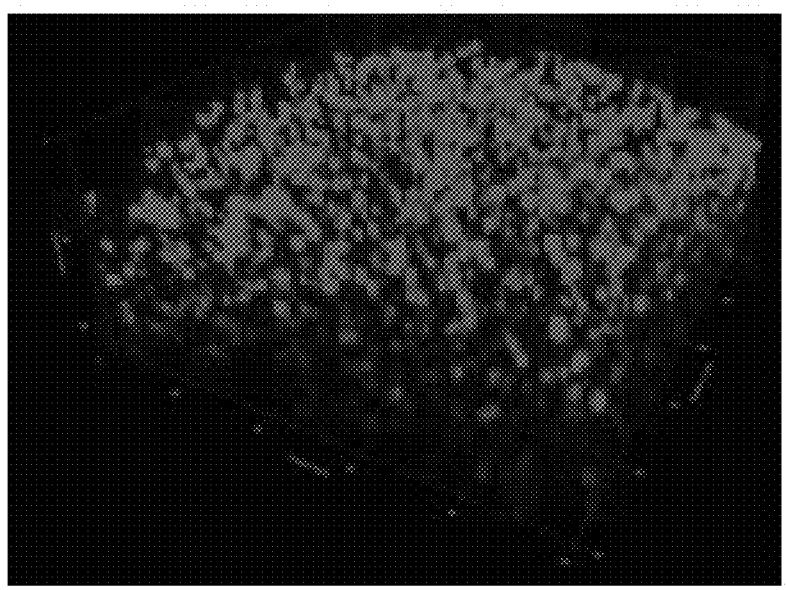
FIG. 8 is a confocal microscopy image illustrating exopolymeric material produced by *S. aureus* and *P. aeruginosa* (red color) mixed nano-biofilm cultured on a chip after 16 h incubation *S. aureus-P. aeruginosa*.
Figure 9:
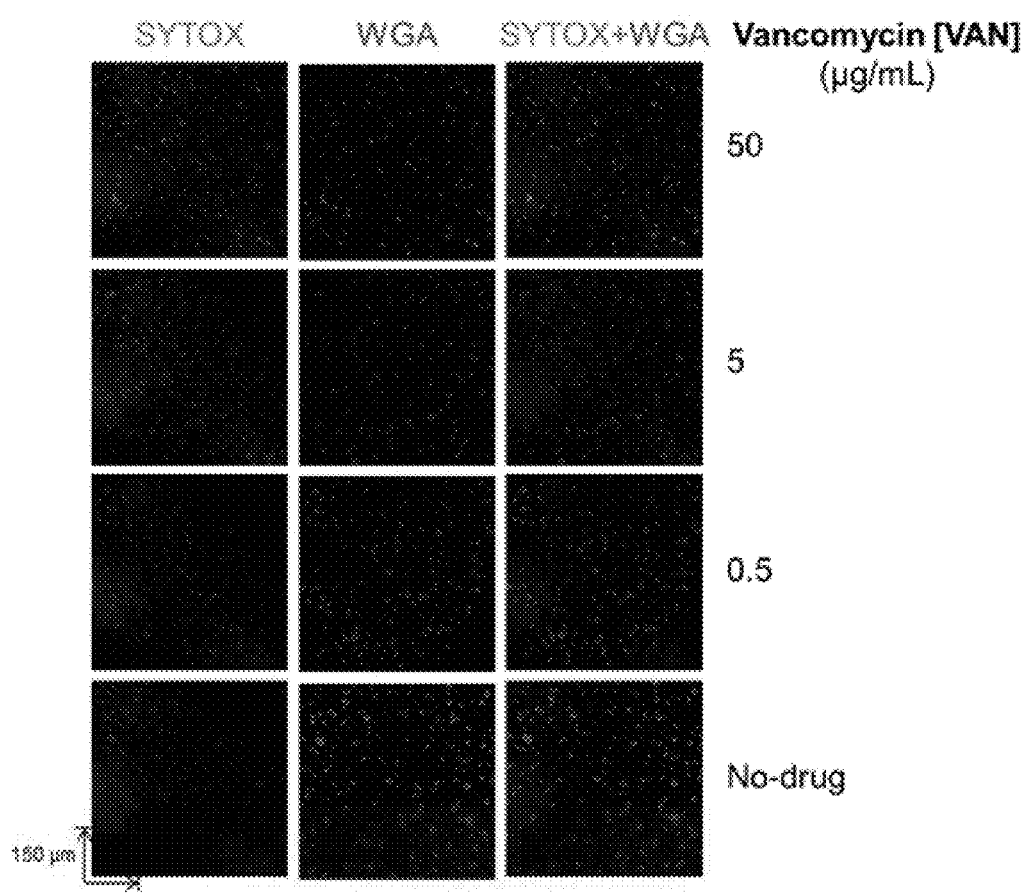
FIG. 9 represents microscopy images illustrating drug-susceptibility of *S. aureus-P. aeruginosa* mixed nano-biofilm against different concentrations of vancomycin. SYTOX (green color-left panel) stains the nucleic acid and chromosome of dead bacteria. Wheat germ agglutinin (WGA) differentially stains gram-positive bacteria (*S. aureus*—red color, middle panel) (right-hand panel shows both SYTOX and WGA; red and green).

Results showing images and testing of antimicrobial activity using the chips of the present example are illustrated in FIGS. 7, 8, and 9, below.

Example 4

Polymicrobial (e.g., Fungi-Bacteria) Biofilm Chip

Although the majority of studies in Microbiology to date have been dominated by the one organism-one disease concept, it is now clear that a large percentage of infections are polymicrobial in nature, and there is evidence that these interactions may modulate the clinical course of infection and impact treatment [11]. Among these, Candida-bacterial interactions have been described [12]. However, one of the factors limiting the analysis of polymicrobial disease has been the lack of appropriate methodologies that allow for testing of different parameters for co-culture of multiple microorganisms. As proof of concept for the applicability of the nano-biochip for polymicrobial culture, the present example provides methodologies and optimized conditions for the nano-scale co-culture of C. albicans with S. aureus; and S. aureus with P. aeruginosa. For example, C. albicans has been described to modulate S. aureus biofilm and facilitate micro-colonies formation and drug-resistance in the case of nosocomial infective endocarditis [12,13]. On the other hand, S. aureus synergizes with P. aeruginosa, and enhances its ability form polymicrobial biofilms characteristic with increased drug-resistance.

For the first time, as described in the present example, polymicrobial species were cultured in nano-scale volume on a single testing device (e.g., chip). The growth conditions, namely, pH, temperature, matrix, media, cell-seeding density and staining were optimized as described below to obtain favorable growth conditions for the polymicrobial chip (Table 5). Any methods not described specifically in the present example are performed as described in Example 1 and/or 2, as appropriate.

TABLE 5

Experimental parameters for polymicrobial nano-biofilm chip [C. albicans-S. aureus biofilm]. All amounts and ranges are approximate

| Design variable | Experimental range |
| --- | --- |
| Alginate | 0.2% |
| Seeding cell density | |
| Fungi | $1 \times 10^4$-$1 \times 10^8$ cells per ml |
| Bacteria | $1 \times 10^4$-$1 \times 10^8$ cells per ml |
| Seeding ratio | 1:10 |

TABLE 5-continued

Experimental parameters for polymicrobial nano-biofilm chip
[*C. albicans-S. aureus* biofilm]. All amounts and ranges are approximate

| Design variable | Experimental range |
|---|---|
| pH | 7.2 |
| Medium | YPD, RPMI |
| Media concentration | 2X YPD + 3X RPMI |
| Serum (10%) | Human |
| Time | 6-48 h |

*BHI, Brain Heart Infusion; RPMI, Rosewell Park Memorial Institute

Nosocomial Infective Endocarditis (NIE) accounts for up to 30% IE cases in the industrialized countries, with a mortality rate from 25-40% [14,15]. The incidence of NIE is common in neonates, elderly and immunocompromised individuals such as patients with rheumatic heart disease, dialysis and prosthetic valves [14,16-19]. The occurrence of these infections can be bacterial or fungal in origin. *Staphylococcus aureus* has been identified to be the primary pathogen of infective endocarditis [20,21]. However, from a greater percentage in occurrence of infections, it is now clear that a large proportion of infections are polymicrobial in nature [22,23].

*Candida-Staphylococcus* interactions have been identified as one of the most frequent microbial consortium in the many clinical conditions [13,23]. In the early phase of (within 60 days) of prosthetic valve endocarditis, *S. aureus-C. albicans* have been isolated as the common etiological agents of IE [21]. In addition, both *S. aureus* and *C. albicans*, upon adhering to biotic or abiotic surfaces, can form biofilms, which are inherently resistant to the antimicrobial treatments compared to their planktonic counterparts [24,25]. The biofilms formed on the native and/or prosthetic aortic valve leaflet disks and begin to serve as a source of bacteremia/fungemia downstream [26,27]. Several synergistic interactions between *S. aureus* and *C. albicans* in multi-species biofilms such as passive drug resistance, metabolic cooperation, quorum sensing, confer competitive advantage to polymicrobial biofilms [28].

Figure 10:
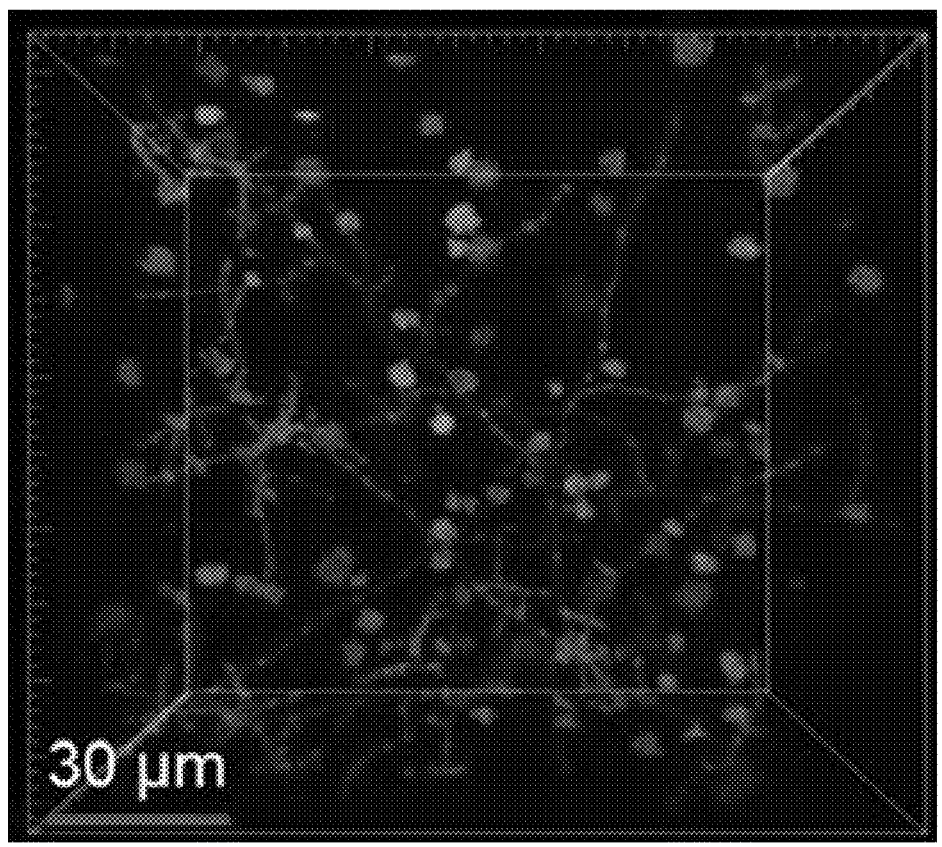
FIG. 10 is a confocal microscopy image of *S. aureus* (yellow cells (rounded, globular shapes)) and *C. albicans* (purple and blue filaments and cells (linear shapes and smaller rounded dots on the filaments) mixed nano-biofilm cultured on a chip after 24 h incubation.

High-Throughput Screening (HTS) using a polymicrobial biofilm chip of the present disclosure will serve as an alternative, where the vast chemical and biological space of leads and targets can be simultaneously and rapidly inspected for effective biomolecules or 'hits' [29]. FIG. 10 portrays a confocal microscopy image of co-culture biofilms containing mixed-species cultures of *C. albicans* and *S. aureus* stained with FUN-1 and concanavalin A (e.g., individual spots on the chip array include two or more species cultures within the spot). The metabolically active yeast cells, pseudohyphae and hyphal filaments of *C. albicans* can be identified as purple-blue strands. The *S. aureus* microcolonies observed as yellow-orange colored spheres were stained by FUN-1.

CONCLUSIONS

The results of the above Examples are consistent with those previously reported for biofilms formed using conventional techniques. This indicates that, despite several thousand-fold miniaturization (compared to biofilms formed using the conventional 96-well microtiter plate model), the nano-scale cultures formed on the biochip display morphological, structural and phenotypic characteristics that are comparable to the biofilms formed using standard methodologies. In some embodiments, the biochip is composed of 1200 equivalent and spatially distinct nano-cultures of 30 nl per spot volume on a single slide, and multiple chips can be printed and processed simultaneously. The hallmarks of this technology are miniaturization and automation, which combine to cut reagent use and analysis times, minimize or eliminate labor intensive steps, and dramatically reduce assay costs.

Thus, the biochip offers several distinct advantages over conventional microbial culture techniques, including truly high-throughput (and even ultra-high-throughput, i.e. the ability to perform >10,000 test per day), rapid and easy handling, and automated analyses; thus potentially revolutionizing microbial culture in the laboratory and opening new avenues of research. Besides the major emphasis on high content screening for antibiotic discovery, its flexibility and adaptability will also make this technique highly valuable in the development and implementation of a number of applications demanding high speed, including phenotype-based assays for microbial identification, high throughput genomics, and possibly to the field of metagenomics and the microbiome project. Owing to the potential of this technology in "accelerated" drug-discovery, this platform is envisioned as a universal technology that can be adapted in the fields of emerging infectious diseases.

In this disclosure, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes maybe reversed, and certain features of the invention maybe utilized independently, all as would be apparent to one skilled in the art after having the benefit of this description of the invention. Changes may be made in the elements described herein without departing from the spirit and scope of the invention as described in the following claims.

REFERENCES

1. Edmond M B, Wallace S E, McClish D K, Pfaller M A, Jones R N, et al. (1999) Nosocomial bloodstream infections in United States hospitals: a three-year analysis. Clin Infect Dis 29: 239-244.
2. Wenzel R P, Edmond M B (2001) The impact of hospital-acquired bloodstream infections. Emerg Infect Dis 7: 174-177.
3. Parahitiyawa N B, Scully C, Leung W K, Yam W C, Jin L J, et al. (2010) Exploring the oral bacterial flora: current status and future directions. Oral Dis 16: 136-145.
4. Boucher H W, Talbot G H, Bradley J S, Edwards J E, Gilbert D, et al. (2009) Bad bugs, no drugs: no ESKAPE! An update from the Infectious Diseases Society of America. Clin Infect Dis 48: 1-12.

5. Kawasumi M, Nghiem P (2007) Chemical genetics: elucidating biological systems with small-molecule compounds. J Invest Dermatol 127: 1577-1584.
6. Vaschetto M, Weissbrod T, Bodle D, Guner O (2003) Enabling high-throughput discovery. Curr Opin Drug Discov Devel 6: 377-383.
7. Wenzel R P (2007) Health care-associated infections: major issues in the early years of the 21st century. Clin Infect Dis 45 Suppl 1: S85-88.
8. Harrison-Balestra C, Cazzaniga A L, Davis S C, Mertz P M (2003) A wound-isolated *Pseudomonas aeruginosa* grows a biofilm in vitro within 10 hours and is visualized by light microscopy. Dermatologic surgery: official publication for American Society for Dermatologic Surgery [et al] 29: 631-635.
9. Church D, Elsayed S, Reid O, Winston B, R. L (2006) Burn Wound Infections. Clin Microbiol Rev 19: 403-434.
10. Lilly H. A., Lowbury E. J., Wilkins M. D., J. S. C (1979) Staphylococcal sepsis in a burns unit. J Hyg (Lond) 83: 429-435.
11. Rogers G B, Hoffman L R, Whiteley M, Daniels T W, Carroll M P, et al. (2010) Revealing the dynamics of polymicrobial infections: implications for antibiotic therapy. Trends Microbiol 18: 357-364.
12. Thein Z M, Seneviratne C J, Samaranayake Y H, Samaranayake L P (2009) Community lifestyle of *Candida* in mixed biofilms: a mini review. Mycoses 52: 467-475.
13. Harriott M M, M C. N (2009) *Candida albicans* and *Staphylococcus aureus* form polymicrobial biofilms: effects on antimicrobial resistance. Antimicrob Agents Chemother 53: 3914-3922.
14. Benito N (2009) Health care-associated native valve endocarditis: importance of non-nosocomial acquisition. Ann Intern Med 150: 586-594.
015. Fernandez-Hidalgo N (2008) Contemporary epidemiology and prognosis of health care-associated infective endocarditis. Clin Infect Dis 47: 1287-1297.
16. Moreillon P, Que Y A (2004) Infective endocarditis. Lancet 363: 139-149.
17.l Lopez J (2010) Age-dependent profile of left-sided infective endocarditis: a 3-center experience. Circulation 121: 892-897.
18. Durante-Mangoni E (2008) Current features of infective endocarditis in elderly patients: results of the International Collaboration on Endocarditis Prospective Cohort Study. Arch Intern Med 168: 2095-2103.
19. Fowler V G (1999) Infective endocarditis due to *Staphylococcus aureus:* 59 prospectively identified cases with follow-up. Clin Infect Dis 28: 106-114.
20. Brusch J (2007) Infective Endocarditis: Management in the Era of Intravascular Devices. Informa Healthcare, New york.
21. Wang A, Athan E, Pappas P A, Fowler V G Jr, Olaison L, et al. (2007) Contemporary clinical profile and outcome of prosthetic valve endocarditis. JAMA 297: 1354-1361.
22. Thein Z M, et al. (2009) Community lifestyle of Candida in mixed biofilms: a mini review. Mycoses 52: 467-475.
23. Rogers G B, et al., (2010) Revealing the dynamics of polymicrobial infections: implications for antibiotic therapy. Trends Microbiol 18: 357-364.
24. Singh R, Ray P, Das A, M S (2010) Penetration of antibiotics through *Staphylococcus aureus* and *Staphylococcus epidermidis* biofilms J Antimicrob Chemother 65: 1955-1958.
25. Chandra J, Mukherjee P, Leidich S, Faddoul F, Hoyer L, et al. (2001) Antifungal resistance of candidal biofilms formed on denture acrylic in vitro. J Dent Res 80: 903-908.
26. Moreillon P, Que Y A, Bayer (2002) Pathogenesis of streptococcal and staphylococcal endocarditis. Infect Dis Clin North Am 16: 297-318.
27. L J. D (2003) *Candida* biofilms and their role in infection. Trends Microbiol 11: 30-36.
28. Wolcott R, Costerton J W, Raoult D a, S J. C (2012) The polymicrobial nature of biofilm infection. Clin Microbiol Infect.
29. Vaschetto M ea (2003) Enabling high-throughput discovery. Curr Opin Drug Discov Devel 6: 377-383.
30. Rolston K V I, G P. B (2006) Infections in patients with cancer. Cancer medicine 7: 2222-2245.
31. Altoparlak U, Erol S, Akcay M N, Celebi F, Kadanali A (2004) The time-related changes of antimicrobial resistance patterns and predominant bacterial profiles of burn wounds and body flora of burned patients. Burns: journal of the International Society for Burn Injuries 30: 660-664.
32. Manson W L, Pernot P C, Fidler V, Sauer E W, Klasen H J (1992) Colonization of burns and the duration of hospital stay of severely burned patients. The Journal of hospital infection 22: 55-63.
33. Wurtz R, Karajovic M, Dacumos E, Jovanovic B, Hanumadass M (1995) Nosocomial infections in a burn intensive care unit. Burns: journal of the International Society for Burn Injuries 21: 181-184.

The invention claimed is:
1. A microbial testing device comprising:
a substrate comprising a flat surface that is coated with a hydrophobic polymer;
a plurality of spatially distinct, three-dimensional culture spots disposed on the hydrophobic polymer, wherein each of the spatially distinct, three-dimensional culture spots comprises:
(i) a mixture of viable microbial cells;
(ii) a matrix material containing a hydrogel selected from the group consisting of: alginate, collagen, matrigel, gelatin, dextran, chitosan, poloxamer, polyethelene glycol, and combinations thereof, such that the substrate comprises a plurality of defined cell-adhesive islands on a cell non-adhesive background; and
(iii) an initial amount of growth medium within each of the spatially distinct, three-dimensional culture spots that is sufficient to form a viable microbial cell culture in each of the spatially distinct, three-dimensional culture spots within 6-24 hours of incubation without exposing the spatially distinct, three-dimensional culture spots on the substrate to additional growth media,
wherein the matrix material at least partially encapsulates the mixture of viable microbial cells and growth medium within the plurality of spatially distinct, three-dimensional culture spots;
wherein the plurality of spatially distinct, three-dimensional culture spots are obtained without submerging the flat surface of the substrate in growth media;
wherein the viable microbial cell cultures in each of the spatially distinct, three-dimensional culture spots develop one or more phenotypic characteristics of a microbial culture biofilm; and
wherein the initial amount of growth medium is present in an amount sufficient to sustain growth and viability of the mixture of microbial cells in the culture spots for at least 24 hours without submerging the spots on the substrate in additional growth media.

2. The testing device of claim 1, wherein the substrate is made of a material selected from the group consisting of: glass, polymer, a metal, a metal alloy, and silicone.

3. The testing device of claim 1, wherein the hydrophobic polymer is selected from the group consisting of: polystyrene-co-maleic anhydride (PSMA), poly-methyl methacrylate, polystyrene, poly-vinyl chloride, an amino siloxane, a methacrylic acid copolymer, a polyolefin, and a combination thereof.

4. The testing device of claim 3, wherein the hydrophobic polymer is polystyrene-co-maleic anhydride (PSMA).

5. The testing device of claim 1, wherein the viable microbial cells are selected from the group consisting of: fungal cells, bacterial cells, and combinations of fungal cells and bacterial cells.

6. The testing device of claim 1, wherein at least one of the plurality of spatially distinct, three-dimensional culture spots on the device comprises a different type of viable microbial cell from at least one other of the plurality of spatially distinct, three-dimensional culture spots.

7. The testing device of claim 6, wherein at least one spot on the device comprises bacterial cells and at least one spot on the device comprises fungal cells.

8. The testing device of claim 1, wherein at least one of the plurality of spatially distinct, three-dimensional culture spots includes at least two different species of viable microbial cells in the at least one of the plurality of spatially distinct, three-dimensional culture spots.

9. The testing device of claim 1, wherein the matrix material hydrogel comprises collagen.

10. The testing device of claim 1, wherein the matrix material hydrogel comprises alginate.

11. The testing device of claim 1, wherein the matrix material includes about 0.055 to about 5% of a hydrogel.

12. The testing device of claim 1, wherein each of the plurality of spatially distinct, three-dimensional culture spots has a seeding density of viable microbial cells of about $1\times10^1$ to about $1\times10^9$ cells per milliliter (ml).

13. The testing device of claim 8, wherein the seeding ratio of the at least two different species of viable microbial cells is about 1:1 to about 1:100.

14. The testing device of claim 1, wherein the pH of the plurality of spatially distinct, three-dimensional culture spots is about 5 to about 8.5.

15. The testing device of claim 1, wherein the growth medium is selected from the group consisting of: Brain Heart Infusion (BHI), Yeast Peptone Dextrose (YPD), Luria Bertani (LB), Tryptic Soy Broth (TSB), Roswell Park Memorial Institute (RPMI), and Mueller Hinton broth (MHB).

16. The testing device of claim 1, wherein each of the plurality of spatially distinct, three-dimensional culture spots has a volume in a nanoliter range.

17. The testing device of claim 16, wherein each of the plurality of spatially distinct, three-dimensional culture spots is less than approximately 100 nanoliters (nL) in volume upon disposition.

18. The testing device of claim 1, wherein each of the plurality of spatially distinct, three-dimensional culture spots further comprises a growth serum.

* * * * *